(12) United States Patent
Hauville et al.

(10) Patent No.: US 12,280,184 B2
(45) Date of Patent: Apr. 22, 2025

(54) METHOD AND APPARATUS FOR PURGING UNWANTED SUBSTANCES FROM AIR

(71) Applicant: FIPAK Research and Development Company, Rowley, MA (US)

(72) Inventors: Francois Hauville, Ipswich, MA (US); Cédric Herry, Val de Reuil (FR)

(73) Assignee: FIPAK Research And Development Company, Rowley, MA (US)

( * ) Notice: Subject to any disclaimer, the term of this patent is extended or adjusted under 35 U.S.C. 154(b) by 115 days.

(21) Appl. No.: 16/688,155

(22) Filed: Nov. 19, 2019

(65) Prior Publication Data

US 2020/0330639 A1 Oct. 22, 2020

Related U.S. Application Data

(63) Continuation of application No. 14/046,641, filed on Oct. 4, 2013, now Pat. No. 10,478,517, which is a
(Continued)

(51) Int. Cl.
*A61L 9/22* (2006.01)
*B01D 53/75* (2006.01)
(Continued)

(52) U.S. Cl.
CPC ............... *A61L 9/22* (2013.01); *B01D 53/75* (2013.01); *B01D 53/90* (2013.01); *B01D 53/323* (2013.01);
(Continued)

(58) Field of Classification Search
CPC ........... A61L 9/22; B01D 53/75; B01D 53/90; B01D 53/323; B01D 53/864;
(Continued)

(56) References Cited

U.S. PATENT DOCUMENTS 3,944,403 A 3/1976 Simpson et al.
4,070,300 A 1/1978 Moroni et al.
(Continued)

FOREIGN PATENT DOCUMENTS

CN 2079081 6/1991
CN 2141873 9/1993
(Continued)

OTHER PUBLICATIONS

Hsiao, M.C. et al., Plasma-assisted decomposition of methanol and trichloroethylene in atmospheric pressure air streams by electrical discharge processing, Journal of Applied Physics, vol. 78, No. 5, 1995, pp. 3451-3456.
(Continued)

*Primary Examiner* — Xiuyu Tai
(74) *Attorney, Agent, or Firm* — Pandiscio & Pandiscio

(57) ABSTRACT

Apparatus comprising:
  a fumehood; and
  an air treatment device for purging unwanted substances from the exhaust air of the fumehood, the air treatment device comprising:
    a non-thermal plasma reactor stage for producing air byproducts comprising O•, N•, OH• and $O_3$ and introducing those air byproducts into the exhaust air of the fumehood so as to treat the exhaust air of the fumehood; and
    a catalyst stage downstream of the non-thermal plasma reactor stage for further treating the air downstream of the non-thermal plasma reactor stage.

11 Claims, 19 Drawing Sheets

Related U.S. Application Data continuation-in-part of application No. 13/793,145, filed on Mar. 11, 2013, now Pat. No. 9,114,338, which is a continuation-in-part of application No. 12/998,134, filed as application No. PCT/US2009/057666 on Sep. 21, 2009, now Pat. No. 9,108,141, which is a continuation of application No. 12/465,434, filed on May 13, 2009, now Pat. No. 8,152,899.

(60) Provisional application No. 61/709,773, filed on Oct. 4, 2012, provisional application No. 61/608,871, filed on Mar. 9, 2012, provisional application No. 61/244,218, filed on Sep. 21, 2009, provisional application No. 61/098,440, filed on Sep. 19, 2008.

(51) Int. Cl.
*B01D 53/90* (2006.01)
*B01D 53/32* (2006.01)
*B01D 53/86* (2006.01)
*B08B 15/02* (2006.01)

(52) U.S. Cl.
CPC ........ *B01D 53/864* (2013.01); *B01D 53/8675* (2013.01); *B01D 2255/1021* (2013.01); *B01D 2255/106* (2013.01); *B01D 2255/2073* (2013.01); *B01D 2255/20761* (2013.01); *B01D 2259/818* (2013.01); *B08B 15/023* (2013.01)

(58) Field of Classification Search
CPC ........ B01D 53/8675; B01D 2255/1021; B01D 2255/106; B01D 2255/2073; B01D 2255/20761; B01D 2259/818; B01D 53/261; B01D 53/8625; B01D 53/56; B01D 2253/106; B01D 2255/20746; B01D 2257/404; B01D 2255/20753; B01D 2255/20723; B01D 2255/104; B01D 2251/104; B01D 2255/20738; B01D 2257/80; B01D 53/865; B01D 53/9431; B01D 53/32; B01D 53/9418; B01D 2255/1025; B01D 2255/2065; B01D 2255/1028; B01D 2255/1023; B01D 2251/2062; B01D 2255/50; B01D 2255/2042; B08B 15/023; B01J 23/34; F01N 2240/28; F01N 2240/25; F01N 13/009; F01N 3/2066; F01N 3/2073
See application file for complete search history.

(56) References Cited

U.S. PATENT DOCUMENTS

| | | |
|---|---|---|
| 4,981,501 A | 1/1991 | Von Blucher et al. |
| 5,288,306 A | 2/1994 | Aibe et al. |
| 5,372,788 A | 12/1994 | Kinoshita et al. |
| 5,486,410 A | 1/1996 | Groeger et al. |
| 5,626,820 A | 5/1997 | Kinkead et al. |
| 5,662,728 A | 9/1997 | Groeger |
| 5,772,738 A | 5/1998 | Muraoka |
| 6,038,853 A | 3/2000 | Penetrante et al. |
| 6,156,089 A | 12/2000 | Stemmer et al. |
| 6,302,946 B1 | 10/2001 | Cronia et al. |
| 6,374,595 B1 | 4/2002 | Penetrante et al. |
| 6,395,144 B1 | 5/2002 | Yi et al. |
| 6,402,819 B1 | 6/2002 | De Ruiter et al. |
| 6,936,094 B2 | 8/2005 | Minemura et al. |
| 7,029,516 B2 | 4/2006 | Campbell et al. |
| 7,093,429 B1 | 8/2006 | Cho |
| 7,132,007 B1 | 11/2006 | Von Blucher et al. |
| 7,226,496 B2 | 6/2007 | Ehlers |
| 7,285,157 B1 | 10/2007 | Dukes et al. |
| 7,347,979 B2 | 3/2008 | Iida et al. |
| 7,517,381 B2 | 4/2009 | Rohrbach et al. |
| 7,648,683 B2 | 1/2010 | Miyairi et al. |
| 7,758,836 B1 | 7/2010 | Huggins et al. |
| 8,152,899 B2 | 4/2012 | Hauville |
| 2001/0002244 A1* | 5/2001 | Gieshoff ............... F01N 3/2073 423/239.1 |
| 2002/0155049 A1* | 10/2002 | Hong ..................... B01J 23/34 423/239.1 |
| 2003/0041733 A1 | 3/2003 | Seguin et al. |
| 2004/0033178 A1 | 2/2004 | Autin et al. |
| 2004/0109800 A1* | 6/2004 | Pahlman ................ B01D 53/83 422/177 |
| 2004/0116025 A1 | 6/2004 | Gogins et al. |
| 2005/0079112 A1 | 4/2005 | Li et al. |
| 2005/0274599 A1 | 12/2005 | Tamura et al. |
| 2006/0042210 A1 | 3/2006 | Dallas et al. |
| 2006/0185336 A1* | 8/2006 | Nakano ............. B01J 20/28023 55/524 |
| 2006/0243134 A1 | 11/2006 | Von Blucher et al. |
| 2007/0014711 A1* | 1/2007 | Deevi ..................... B01J 23/72 131/334 |
| 2007/0045101 A1 | 3/2007 | Ogut et al. |
| 2008/0010959 A1 | 1/2008 | Gillingham et al. |
| 2008/0110342 A1 | 5/2008 | Ensor et al. |
| 2008/0115670 A1 | 5/2008 | Hauville |
| 2009/0221047 A1 | 9/2009 | Schindler et al. |
| 2009/0324443 A1 | 12/2009 | Whitehead et al. |
| 2010/0089240 A1 | 4/2010 | Krichtafovitch |
| 2010/0172793 A1 | 7/2010 | Obee et al. |
| 2011/0038771 A1 | 2/2011 | Buelow et al. |
| 2011/0259191 A1 | 10/2011 | Hauville |

FOREIGN PATENT DOCUMENTS

| | | |
|---|---|---|
| CN | 201154290 | 11/2008 |
| CN | 102215941 | 10/2011 |
| EP | 1666152 | 6/2006 |
| EP | 1738817 | 1/2007 |
| EP | 2759330 | 7/2014 |
| GB | 2352987 | 10/1999 |
| JP | S50-032089 | 3/1975 |
| JP | H4-271831 | 9/1992 |
| JP | H05-228365 | 9/1993 |
| JP | H05-277336 | 10/1993 |
| JP | H6-190236 | 7/1994 |
| JP | H07-299319 | 11/1995 |
| JP | H09-38449 | 2/1997 |
| JP | H10-0244149 | 9/1998 |
| JP | H11-226338 | 8/1999 |
| JP | 2000-167034 | 6/2000 |
| JP | 2000-262844 | 9/2000 |
| JP | 2000-334244 | 12/2000 |
| JP | 2001-252522 | 9/2001 |
| JP | 2001-524609 | 12/2001 |
| JP | 2002-506389 | 2/2002 |
| JP | 2002-177717 | 6/2002 |
| JP | 2002-224559 | 8/2002 |
| JP | 2003-010625 | 1/2003 |
| JP | 2003-080058 | 3/2003 |
| JP | 2003-512148 | 4/2003 |
| JP | 2003-305333 | 10/2003 |
| JP | 2004-176703 | 6/2004 |
| JP | 2005-172412 | 6/2005 |
| JP | 2006-102705 | 4/2006 |
| JP | 2006-167220 | 6/2006 |
| JP | 2007-100578 | 4/2007 |
| JP | 2007-268165 | 10/2007 |
| JP | 2008-036080 | 2/2008 |
| JP | 2008-036169 | 2/2008 |
| JP | 2008-504094 | 2/2008 |
| JP | 2009-101333 | 5/2009 |
| JP | 2009-519819 | 5/2009 |
| JP | 2009-148614 | 7/2009 |
| JP | 2009-285654 | 12/2009 |
| JP | 2010-007871 | 1/2010 |
| JP | 2011-233381 | 11/2011 |
| JP | 2012-061393 | 3/2012 |
| WO | WO 91/12737 | 9/1991 |

(56) References Cited

FOREIGN PATENT DOCUMENTS

| WO | WO 01/00301 | 1/2001 |
|---|---|---|
| WO | WO 01/28657 | 4/2001 |
| WO | WO 02/066145 | 8/2002 |
| WO | WO 03/026794 | 4/2003 |
| WO | WO 2006/060417 | 6/2006 |
| WO | WO 2007/009336 | 1/2007 |
| WO | WO 2007/146201 | 12/2007 |
| WO | WO 2009/000229 | 12/2008 |
| WO | WO 2009/002294 | 12/2008 |
| WO | WO 2009/146201 | 12/2009 |
| WO | WO 2010/033905 | 3/2010 |
| WO | WO 2010/094304 | 8/2010 |

OTHER PUBLICATIONS

Jo, Jin Oh et al., Plasma-assisted Catalysis for the Abatement of Isopropyl Alcohol over Metal Oxides, Clean Technology, vol. 20, No. 4, 2014, pp. 375-382.

Ognier, Stephanie et al., Aromatic VOC Removal by Formation of Microparticles in Pure Nitrogen Discharge Barrier Discharge, Plasma Processes and Polymers, vol. 4, No. 5, 2007, pp. 528-536.

Schiorlin, Milko et al., Comparison of Toluene Removal in Air at Atmospheric Conditions by Different Corona Discharges, Environmental Science & Technology, vol. 43, No. 24, 2009, pp. 9386-9392.

Sugasawa, Masami et al., Additive Effect of Water on the Decomposition of VOCs in Nonthermal Plasma, IEEE Transactions on Industry Applications, vol. 46, No. 5, 2010, pp. 1692-1698.

Xinbo, Zhu et al., Catalyst screening for acetone removal in a single-stage plasma-catalysis system, Catalysis Today, vol. 256, 2015, pp. 108-114.

\* cited by examiner

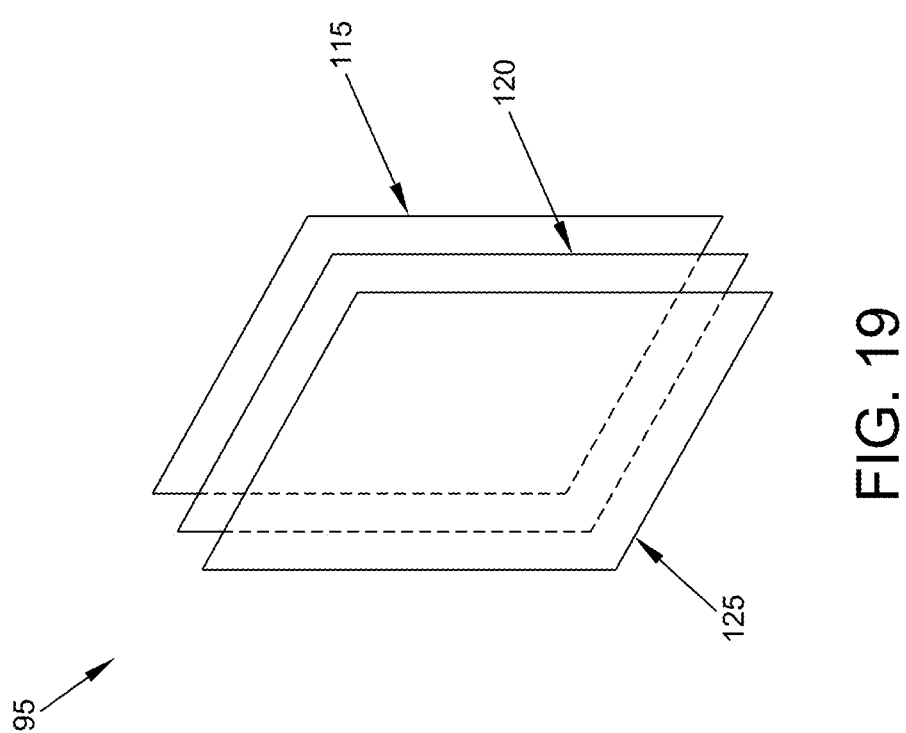

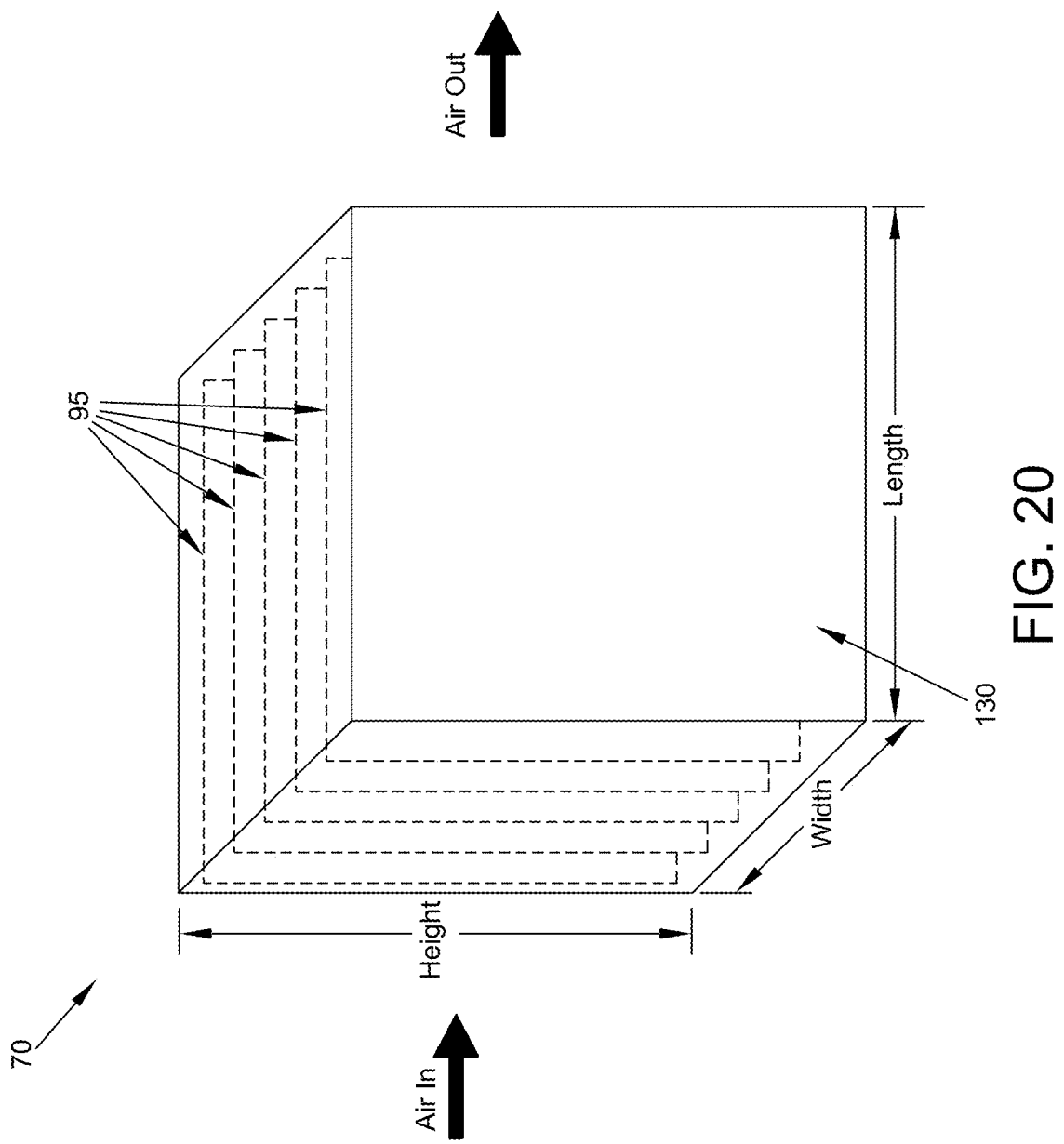

METHOD AND APPARATUS FOR PURGING UNWANTED SUBSTANCES FROM AIR

REFERENCE TO PENDING PRIOR PATENT APPLICATIONS

This patent application is a continuation of pending prior U.S. patent application Ser. No. 14/046,641, filed Oct. 4, 2013 by FIPAK Research and Development Company for METHOD AND APPARATUS FOR PURGING UNWANTED SUBSTANCES FROM AIR, which patent application:

(1) is a continuation-in-part of prior U.S. patent application Ser. No. 13/793,145, filed Mar. 11, 2013 by Francois Hauville for METHOD AND APPARATUS FOR PURGING UNWANTED SUBSTANCES FROM AIR, which patent application:

(i) is itself a continuation-in-part of prior U.S. patent application Ser. No. 12/998,134, filed Mar. 21, 2011 by Francois Hauville for METHOD AND APPARATUS FOR PURGING UNWANTED SUBSTANCES FROM AIR, which patent application in turn claims benefit of prior International (PCT) Patent Application No. PCT/US2009/057666, filed Sep. 21, 2009 by Francois Hauville for METHOD AND APPARATUS FOR PURGING UNWANTED SUBSTANCES FROM AIR, which patent application in turn claims benefit of (a) prior U.S. Provisional Patent Application Ser. No. 61/098,440, filed Sep. 19, 2008 by Francois Hauville for METHOD AND APPARATUS FOR PURGING UNWANTED SUBSTANCES FROM AIR AND/OR NEUTRALIZING UNWANTED SUBSTANCES IN AIR, (b) prior U.S. Provisional Patent Application Ser. No. 61/244,218, filed Sep. 21, 2009 by Francois Hauville for METHOD AND APPARATUS FOR PURGING UNWANTED SUBSTANCES FROM AIR, and (c) prior U.S. Non-Provisional patent application Ser. No. 12/465,434, filed May 13, 2009 by Francois Hauville for METHOD AND APPARATUS FOR PURGING UNWANTED SUBSTANCES FROM AIR; and (ii) claims benefit of prior U.S. Provisional Patent Application Ser. No. 61/608,871, filed Mar. 9, 2012 by Francois Hauville for METHOD AND APPARATUS FOR PURGING AMMONIA AND/OR OTHER TARGET CHEMICALS FROM AIR; and (2) claims benefit of prior U.S. Provisional Patent Application Ser. No. 61/709,773, filed Oct. 4, 2012 by Francois Hauville et al. for NOVEL TWO-STAGE AIR TREATMENT DEVICE COMPRISING A NON-THERMAL PLASMA REACTOR STAGE FOLLOWED BY A CATALYST STAGE.

The nine (9) above-identified patent applications are hereby incorporated herein by reference.

FIELD OF THE INVENTION

This invention relates to air treatment devices in general, and more particularly to air treatment devices of the sort which purge unwanted substances from air, i.e., to air treatment devices which remove unwanted substances from air and/or neutralize unwanted substances in air and/or convert unwanted substances in air to more acceptable substances.

BACKGROUND OF THE INVENTION

Air filters are used to purge unwanted substances from air. By way of example but not limitation, air filters are commonly used in laboratories to purge unwanted substances from the air in fumehoods before the air is vented from the fumehood, e.g., to the atmosphere (in the case of a ducted fumehood) or to the ambient air of the laboratory (in the case of a ductless fumehood).

In the laboratory application noted above, the air filter typically uses activated carbon granules to purge unwanted substances from the air. Activated carbon granules are generally preferred for use in air filters because the activated carbon granules are very effective in purging solvents from the air. Furthermore, the use of activated carbon granules is generally highly advantageous, since the activated carbon granules are easily handled, and since they naturally pack into an enclosure with spaces therebetween so as to provide high surface area contact with excellent air flow. Typically, the activated carbon granules are disposed in a simple filter frame, captured between two opposing screens (e.g., meshes, grills, etc.) which pass air therethrough but retain the activated carbon granules therebetween.

While activated carbon granules are extremely effective in purging solvents from the air, they are largely ineffective in purging acids from the air. As a result, where acids may be used within a fumehood, special additives (e.g., rare earth metals, organic metal catalysts, etc.) must be added to the activated carbon granules in order to purge acids from the air. However, these additives tend to reduce the effective surface area of the activated carbon granules, thereby reducing filter capacity. Furthermore, these acid-purging additives are generally only modestly effective in purging acids from the air, and in many cases can include relatively toxic materials which may be released in the air by the air flow through the filter.

Thus it will be seen that incorporating acid-purging additives with the activated carbon granules results in an air filter with reduced efficiency for purging solvents and which has only modest effectiveness for purging acids.

Thus there is a need for a new and improved air filter which is highly effective in purging both solvents and acids from the air and which works with high efficiency and without using toxic additives.

SUMMARY OF THE INVENTION

These and other objects of the present invention are addressed by the provision and use of a novel air filter which comprises at least two stages, an acid-purging stage and a solvent-purging stage. The acid-purging stage generally comprises an air-permeable skeleton having an acid-neutralizing substance mounted thereto. The solvent-purging stage generally comprises solvent-purging granules packed between two opposing screens (e.g., meshes, grills, etc.).

In one preferred form of the invention, there is provided an air filter for purging unwanted substances from air, the air filter comprising:

an acid-purging stage; and a solvent-purging stage.

In another preferred form of the invention, there is provided an air filter for purging unwanted substances from air, the air filter comprising:

an acid-purging stage, wherein the acid-purging stage comprises an air-permeable skeleton which has an acid-neutralizing substance mounted thereto, wherein the air-permeable skeleton comprises fiberglass fibers and the acid-neutralizing substance comprises sodium bicarbonate, and further wherein the sodium bicarbonate is secured to the fiberglass fibers using an adhesive; and a solvent-purging stage, wherein the solvent-purging stage comprises solvent-purging granules captured between two air-permeable screens, and further wherein the solvent-purging granules comprise activated carbon granules.

In another preferred form of the invention, there is provided an air filter for purging unwanted substances from air, the air filter comprising:
an acid-purging stage, wherein the acid-purging stage comprises an air-permeable skeleton which has an acid-neutralizing substance mounted thereto, wherein the air-permeable skeleton comprises open cell polyurethane foam and the acid-neutralizing substance comprises sodium bicarbonate, and further wherein the sodium bicarbonate is secured to the open cell polyurethane foam using an adhesive; and
a solvent-purging stage, wherein the solvent-purging stage comprises solvent-purging granules captured between two air-permeable screens, and further wherein the solvent-purging granules comprise activated carbon granules.

In another preferred form of the invention, there is provided a method for purging unwanted substances from air, the method comprising:
providing an air filter for purging unwanted substances from air, the air filter comprising:
an acid-purging stage; and
a solvent-purging stage; and
passing the air which is to be filtered through the air filter so as to purge unwanted substances from the air.

And in another preferred form of the invention, there is provided a method for purging unwanted substances from air, the method comprising:
providing an air filter for purging unwanted substances from air, the air filter comprising:
an acid-purging stage, wherein the acid-purging stage comprises an air-permeable skeleton which has an acid-neutralizing substance mounted thereto, wherein the air-permeable skeleton comprises fiberglass fibers and the acid-neutralizing substance comprises sodium bicarbonate, and further wherein the sodium bicarbonate is secured to the fiberglass fibers using an adhesive; and
a solvent-purging stage, wherein the solvent-purging stage comprises solvent-purging granules captured between two air-permeable screens, and further wherein the solvent-purging granules comprise activated carbon granules; and
passing the air which is to be filtered through the air filter so as to purge unwanted substances from the air.

And in another preferred form of the invention, there is provided a method for purging unwanted substances from air, the method comprising:
providing an air filter for purging unwanted substances from air, the air filter comprising:
an acid-purging stage, wherein the acid-purging stage comprises an air-permeable skeleton which has an acid-neutralizing substance mounted thereto, wherein the air-permeable skeleton comprises open cell polyurethane foam and the acid-neutralizing substance comprises sodium bicarbonate, and further wherein the sodium bicarbonate is secured to the open cell polyurethane foam using an adhesive; and
a solvent-purging stage, wherein the solvent-purging stage comprises solvent-purging granules captured between two air-permeable screens, and further wherein the solvent-purging granules comprise activated carbon granules; and
passing the air which is to be filtered through the air filter so as to purge unwanted substances from the air.

In another preferred form of the invention, there is provided an air filter for purging unwanted substances from air, the air filter comprising:
a filtration media; and
at least one reactant attached to the filtration media.

In another preferred form of the invention, there is provided a method for purging unwanted substances from air, the method comprising:
providing an air filter comprising:
a filtration media; and
at least one reactant attached to the filtration media; and
passing the air which is to be filtered through the air filter so as to purge unwanted substances from the air.

In another preferred form of the invention, there is provided apparatus comprising:
a fumehood; and
an air treatment device for purging unwanted substances from the exhaust air of the fumehood, the air treatment device comprising:
a non-thermal plasma reactor stage for producing air byproducts comprising O•, N•, OH• and $O_3$ and introducing those air byproducts into the exhaust air of the fumehood so as to treat the exhaust air of the fumehood; and
a catalyst stage downstream of the non-thermal plasma reactor stage for further treating the air downstream of the non-thermal plasma reactor stage.

In another preferred form of the invention, there is provided a method comprising:
providing apparatus comprising:
a fumehood; and
an air treatment device for purging unwanted substances from the exhaust air of the fumehood, the air treatment device comprising:
a non-thermal plasma reactor stage for producing air byproducts comprising O•, N•, OH• and $O_3$ and introducing those air byproducts into the exhaust air of the fumehood so as to treat the exhaust air of the fumehood; and
a catalyst stage downstream of the non-thermal plasma reactor stage for further treating the air downstream of the non-thermal plasma reactor stage; and
operating the fumehood, including passing the exhaust air of the fumehood through the air treatment device.

In another preferred form of the invention, there is provided an air treatment device for purging unwanted substances from air, the novel air treatment device comprising:
a non-thermal plasma reactor stage; and
a catalyst stage, wherein the catalyst stage comprises $MnO_2$.

In another preferred form of the invention, there is provided a method for purging unwanted substances from air, the method comprising:
providing an air treatment device for purging unwanted substances from air, the air treatment device comprising:
a non-thermal plasma reactor stage; and
a catalyst stage, wherein the catalyst stage comprises $MnO_2$; and
passing air through the air treatment device.

In another preferred form of the invention, there is provided an air treatment device for purging unwanted substances from air, the air treatment device comprising:
a non-thermal plasma reactor stage, wherein the non-thermal plasma reactor stage comprises a plurality of non-thermal plasma reactor units, wherein the plurality of nonthermal plasma reactor units are arranged substantially adjacent to one another and substantially parallel to one another in an array having a cross-section which defines the effective working area of the non-thermal plasma reactor stage; and
  a catalyst stage.

In another preferred form of the invention, there is provided a method for purging unwanted substances from air, the method comprising:
  providing an air treatment device comprising:
    a non-thermal plasma reactor stage, wherein the non-thermal plasma reactor stage comprises a plurality of non-thermal plasma reactor units, wherein the plurality of non-thermal plasma reactor units are arranged substantially adjacent to one another and substantially parallel to one another in an array having a cross-section which defines the effective working area of the non-thermal plasma reactor stage; and
    a catalyst stage; and
  passing air through the air treatment device.

In another preferred form of the invention, there is provided an air treatment device for purging unwanted substances from air, the air treatment device comprising:
  a treatment passageway having an upstream end for admitting the air which is to be treated and a downstream end for discharging the air which has been treated;
  a side passageway communicating with the treatment passageway intermediate the upstream end of the treatment passageway and the downstream end of the treatment passageway;
  a non-thermal plasma reactor stage communicating with the side passageway for producing air byproducts comprising O•, $O_3$ and OH• and introducing those air byproducts into the treatment passageway; and
  a catalyst stage disposed within the treatment passageway downstream of the side passageway.

In another preferred form of the invention, there is provided a method for purging unwanted substances from air, the method comprising:
  providing an air treatment device comprising:
    a treatment passageway having an upstream end for admitting the air which is to be treated and a downstream end for discharging the air which has been treated;
    a side passageway communicating with the treatment passageway intermediate the upstream end of the treatment passageway and the downstream end of the treatment passageway;
    a non-thermal plasma reactor stage communicating with the side passageway for producing air byproducts comprising O•, $O_3$ and OH• and introducing those air byproducts into the treatment passageway; and
    a catalyst stage disposed within the treatment passageway downstream of the side passageway; and
  passing air through the air treatment device.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:
FIGS. 16-19 are schematic views showing alternative forms of non-thermal plasma reactor units which may be used with the novel two-stage air treatment device of the present invention;
and
  FIG. 20 is a schematic view showing an alternative form of non-thermal plasma reactor stage.

DETAILED DESCRIPTION OF THE PREFERRED EMBODIMENTS

1. Air Filter Comprising an Acid-Purging Stage and a Solvent-Purging Stage 1.1 In General The present invention provides a new and improved air filter which is effective for purging both solvents and acids from the air with high efficiency. To this end, and looking now at FIGS. 1 and 1A, there is shown a novel air filter 5 formed in accordance with the present invention. Air filter 5 generally comprises two stages, an acid-purging stage 10 followed by a solvent-purging stage 15.

Figure 4:
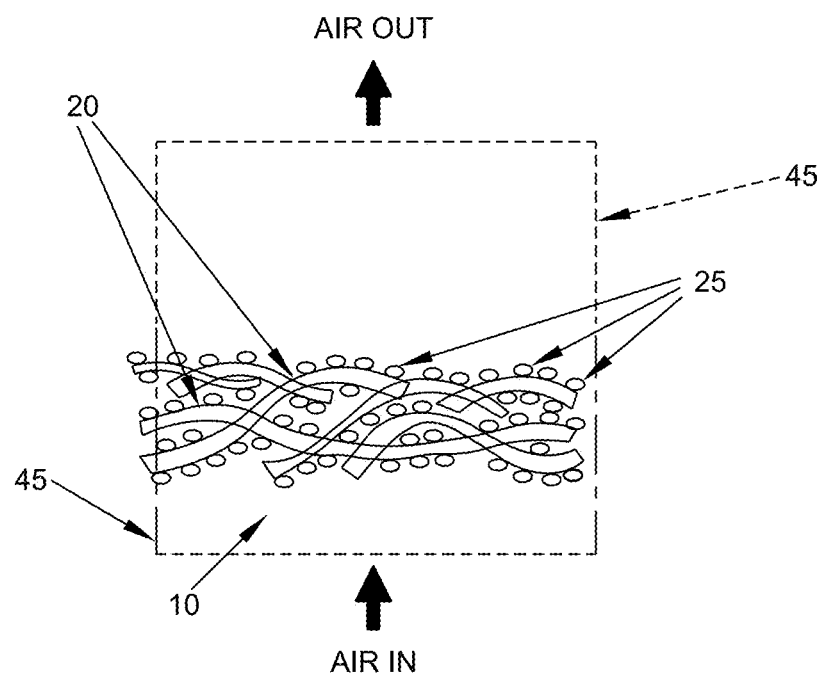

Acid-purging stage 10 generally comprises an air-permeable skeleton 20 (see, for example, FIG. 4) having an acid-neutralizing substance 25 (see, for example, FIG. 4) mounted thereto. In one preferred form of the invention, and looking now at FIG. 1, acid-purging stage 10 comprises fibers (e.g., fiberglass fibers) which have sodium bicarbonate adhered thereto. In another preferred form of the invention, and looking now at FIG. 1A, acid-purging stage 10 comprises an open cell foam (e.g., open cell polyurethane foam) with sodium bicarbonate adhered thereto.

Solvent-purging stage 15 generally comprises solvent-purging granules 30 (see, for example, FIG. 5) packed between two opposing, air-permeable screens (e.g., meshes, grills, etc.) 35. In one preferred form of the invention, the solvent-purging granules comprise activated carbon granules.

As a result of this construction, when air is passed through air filter 5, the air first passes through acid-purging stage 10, where acid-neutralizing substance 25 (e.g., sodium bicarbonate) effectively neutralizes any acids which may be present in the air. Thereafter, the air passes through solvent-purging stage 15, where solvent-purging granules 30 (e.g., activated carbon granules) purge any solvents which may be present in the air.

1.2 Acid-Purging Stage

Looking next at FIGS. 1, 1A and 2-4, acid-purging stage 10 generally comprises an air-permeable skeleton 20 (e.g., fibers, open cell foam, etc.) having an acid-neutralizing substance 25 (e.g., sodium bicarbonate) mounted thereto.

Figure 1:
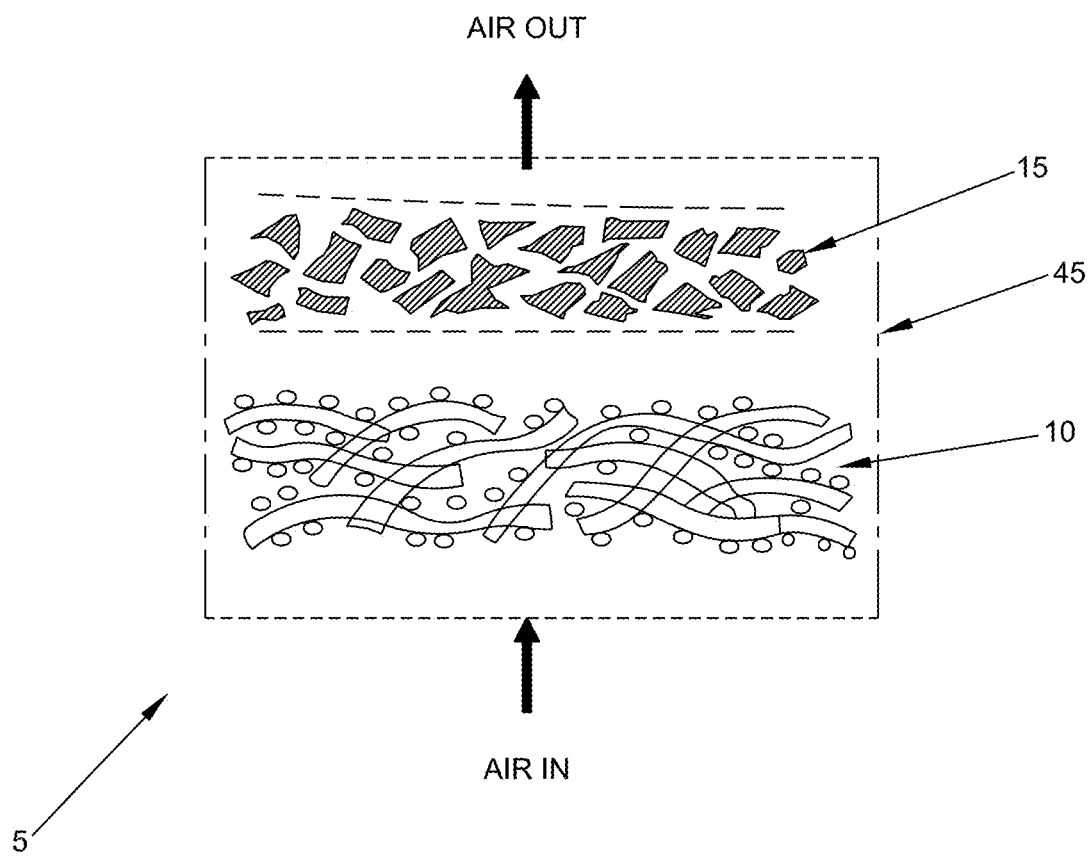
FIG. 1 is a schematic view showing a novel air filter formed in accordance with the present invention.

In one preferred form of the invention, and looking now at FIG. 1, acid-purging stage 10 comprises fiberglass fibers which have sodium bicarbonate adhered thereto. Sodium bicarbonate is extremely effective in neutralizing acids, and is relatively inexpensive, but its powder-like consistency makes it difficult to use in an air filter, where high surface area contact is required. The present invention solves this difficulty, and makes it practical to use sodium bicarbonate in an air filter, by providing a new and improved method for supporting the sodium bicarbonate in an acid-purging stage.

Figure 2:
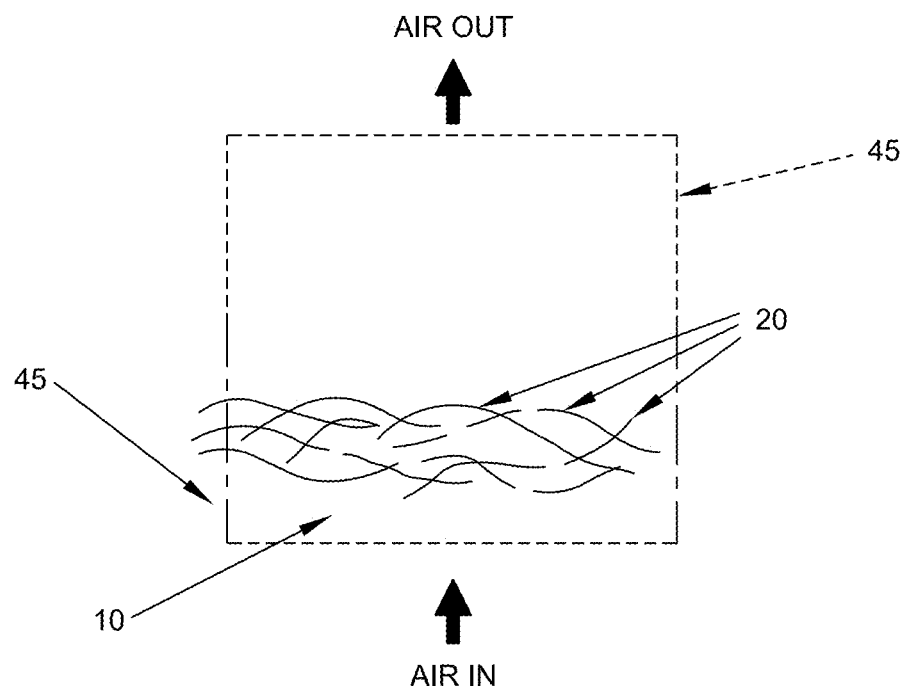
FIGS. 2-4 are schematic views showing how the acid-purging stage of the novel air filter of FIG. 1 can be fabricated.
Figure 3:
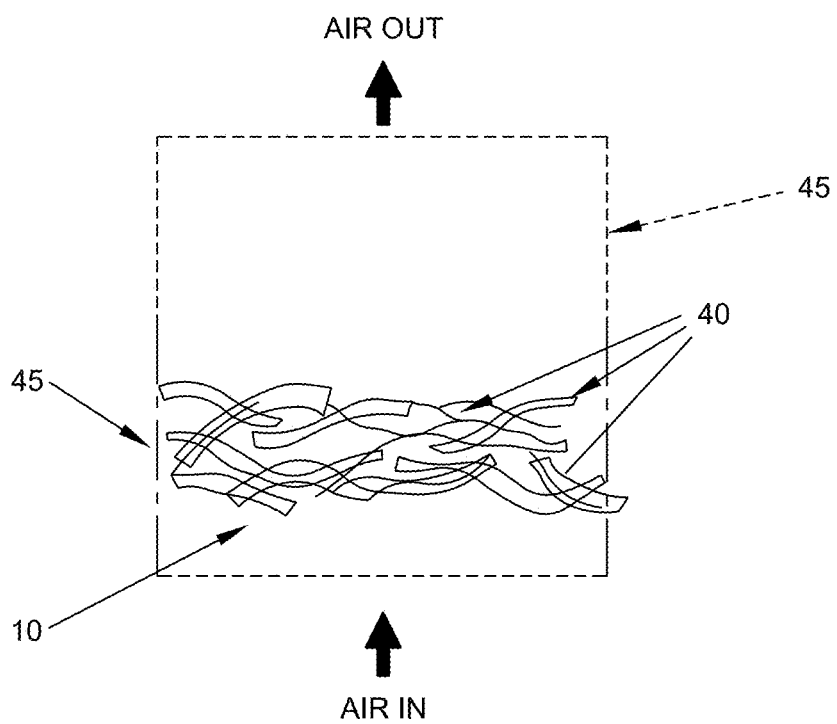

More particularly, and looking now at FIG. 2, acid-purging stage 10 preferably comprises an air-permeable mass of fiberglass fibers which together create the air-permeable skeleton 20. These fiberglass fibers are highly resistant to acids and bases, and easily pass air therethrough with nominal pressure loss. Looking next at FIG. 3, the fiberglass fibers are coated with an adhesive 40. Then, and looking now at FIG. 4, sodium bicarbonate powder is deposited on the fiberglass fibers, with adhesive 40 binding the sodium bicarbonate powder to the fiberglass fibers.

Thus it will be seen that the sodium bicarbonate is interspersed throughout, and adheres to, air-permeable skeleton 20, so that air passing therethrough makes excellent surface area contact with the sodium bicarbonate, whereupon the sodium bicarbonate can neutralize acids in the air.

If desired, acid-purging stage 10 can comprise an air-permeable skeleton 20 made with a structure and/or a material other than, or in addition to, fiberglass fibers (e.g., polyurethane fibers, an open cell foam, etc.), and/or acid-purging stage 10 can comprise an acid-neutralizing substance 25 other than, or in addition to, sodium bicarbonate (e.g., sodium hydroxide, potassium hydroxide, sodium carbonate, calcium carbonate, calcium bicarbonate, calcium hydroxide, etc.).

Figure 1A:
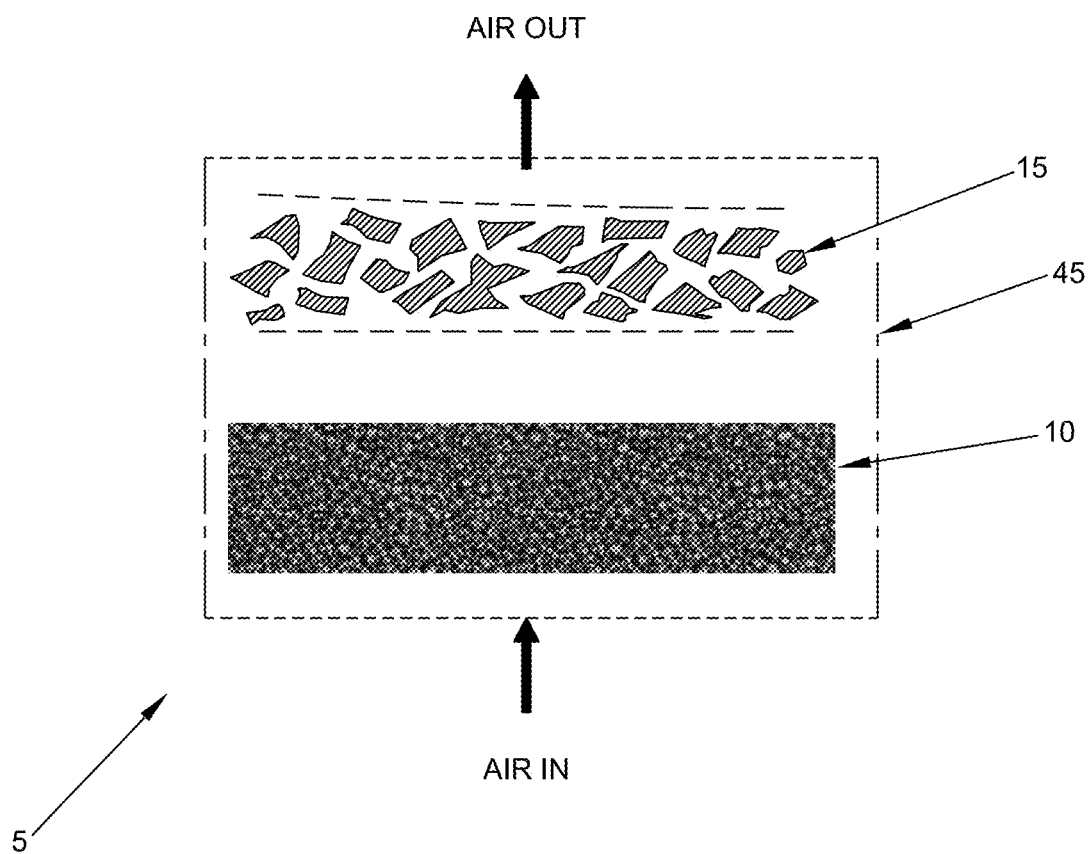
FIG. 1A is a schematic view showing another novel air filter formed in accordance with the present invention.

Thus, in another preferred form of the invention, and looking now at FIG. 1A, acid-purging stage 10 comprises an open cell foam with an acid-neutralizing substance adhered thereto. By way of example but not limitation, acid-purging stage 10 preferably comprises open cell polyurethane foam (preferably having a pore characteristic of 20 PPI, i.e., 20 pores per inch), having sodium bicarbonate adhered thereto. This open cell polyurethane foam is highly resistant to a wide range of acids and bases, and easily passes air therethrough with nominal pressure loss.

1.3 Solvent-Purging Stage

Figure 5:
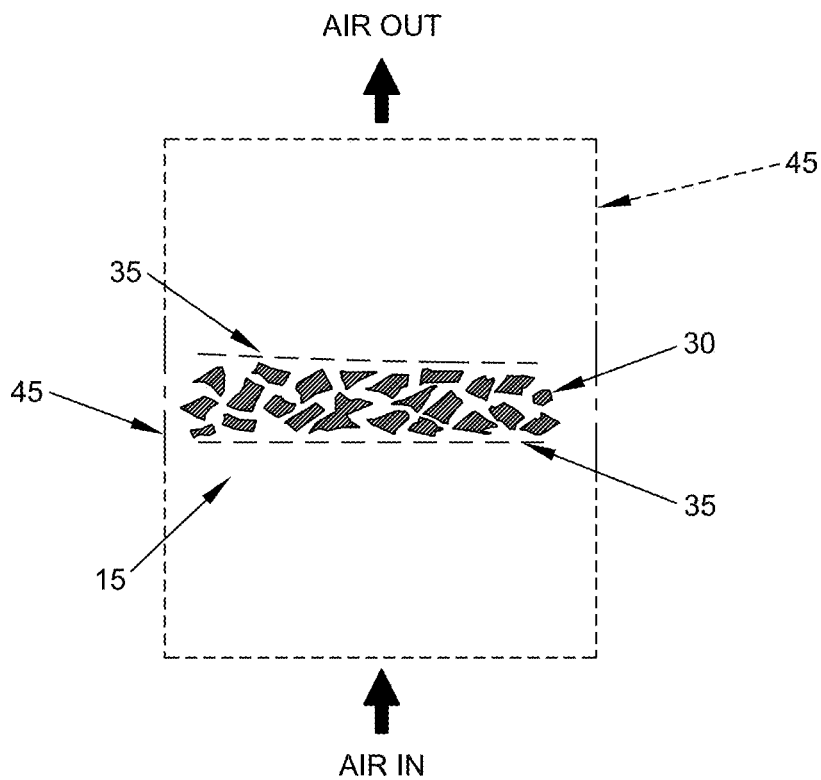
FIG. 5 is a schematic view showing further details of the solvent-purging stage of the novel air filter of FIGS. 1 and 1A.

Looking now at FIG. 5, solvent-purging stage 15 generally comprises solvent-purging granules 30 packed between two opposing air-permeable screens (e.g., meshes, grills, etc.) 35. In one preferred form of the invention, the solvent-purging granules comprise activated carbon granules captured between two opposing air-permeable screens (e.g., meshes, grills, etc.) which pass air therethrough but retain the activated carbon granules therebetween.

1.4 Two-Stage Construction

Figure 5A:
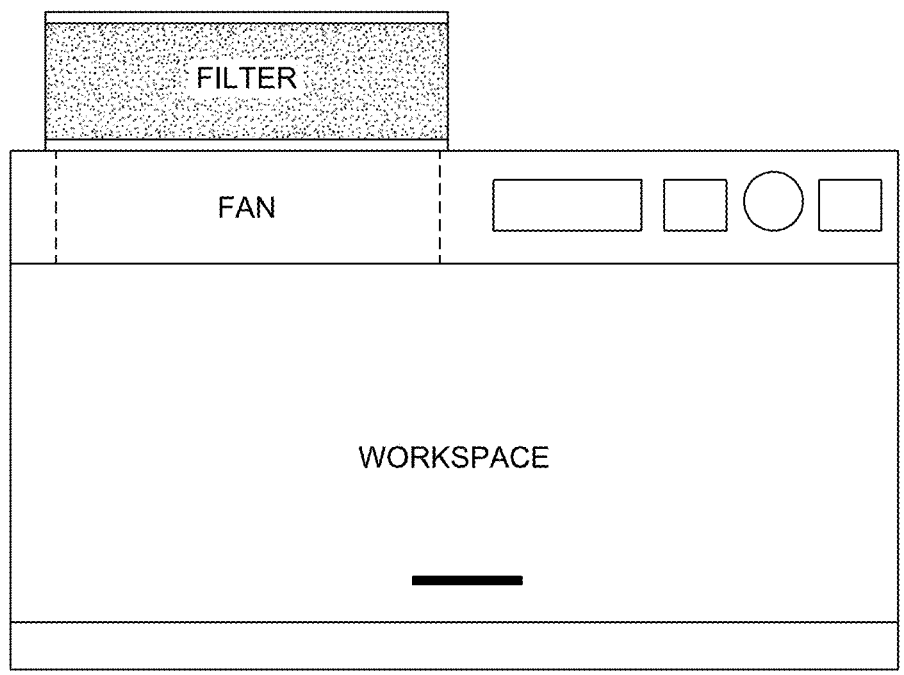
FIG. 5A is a schematic view showing an exemplary ductless fumehood with which the novel air treatment devices of the present invention may be used.

Returning now to FIG. 1, it will be seen that novel air filter 5 comprises a filter frame 45 having mounted therein two filter stages, i.e., acid-purging stage 10 followed by solvent-purging stage 15. Filter frame 45 is sized and configured for appropriate mounting in a fumehood, e.g., a ductless fumehood such as is shown in FIG. 5A. In other words, the "form factor" (Width×Height×Length) of filter frame 45 is compatible with the fumehood with which it is to be used. Among other things, filter frame 45 has a cross-section (i.e., Width×Height) which is equal to the area of the airflow which is to be treated by air filter 5. Acid-purging stage 10 comprises the air-permeable skeleton 20 (preferably fiberglass fibers or an open cell polyurethane foam) which has the acid-neutralizing substance 25 (preferably sodium bicarbonate) mounted thereto. Solvent-purging stage 15 comprises the solvent-purging granules 30 (preferably activated carbon granules). As a result of this construction, when air (e.g., from a ductless fumehood) is passed through air filter 5, the air first passes through acid-purging stage 10, where acid-neutralizing substance 25 (e.g., sodium bicarbonate) neutralizes acids which may be present in the air. Thereafter, the air passes through solvent-purging stage 15, where solvent-purging granules 30 (e.g., activated carbon granules) purge solvents which may be present in the air. Thus, the novel air filter of the present invention is capable of purging both acids and solvents from the air passing through the filter.

Significantly, the foregoing construction provides substantial advantages over the prior art, since it separates the acid-purging operation from the solvent-purging operation, embodying each operation in a separate stage of a singular filter frame, thereby allowing each operation to be optimized for its own particular purpose without detracting from the other operation.

More particularly, the acid-purging stage of the present invention is optimized by, preferably, using highly effective and relatively inexpensive sodium bicarbonate, supported on an air-permeable skeleton structure (e.g., fiberglass fibers, an open cell polyurethane foam, etc.) 20, to neutralize acid. In this respect it should be appreciated that sodium bicarbonate is significantly more effective in neutralizing acids from air than the rare earth metals and organic metal catalysts traditionally used in air filters to purge acids from the air. Significantly, the use of sodium bicarbonate in the air filter also eliminates the toxicity concerns which can be present when using the rare earth metals and organic metal catalysts of the prior art.

Furthermore, the solvent-purging stage of the present invention is optimized by, preferably, using highly effective activated carbon granules to purge solvents from air, but without the addition of the aforementioned acid-purging rare earth metals and organic metal catalysts which can reduce the solvent-purging capacity thereof.

1.5 Reversing the Order of the Stages

In the preceding discussion, acid-purging stage 10 precedes solvent-purging stage 15 in the air flow, i.e., air moving through the air filter moves through acid-purging stage 10 before it moves through solvent-purging stage 15. However, it will be appreciated that, if desired, the acid-purging stage can follow the solvent-purging stage, i.e., air moving through the air filter can move through the solvent-purging stage before it moves through the acid-purging stage.

1.6 Further Aspects of the Novel Air Filter Comprising an Acid-Purging Stage and a Solvent-Purging Stage Thus it will be seen that the present invention is unique in a number of ways, including (i) the two-stage composite construction of the air filter, which combines an acid-purging stage with a solvent-purging stage, (ii) the use of sodium bicarbonate in an air filter, and (iii) the manner in which the sodium bicarbonate is supported within the air filter (e.g., on an air permeable skeleton such as fiberglass fibers, open cell polyurethane foam, etc.).

Furthermore, the present invention purges acids from the air without requiring the use of toxic additives (e.g., rare earth metals, metal catalysts, etc.).

And the present invention purges unwanted acids from the air without diminishing the capacity of the air filter to purge solvents from the air.

Also, the present invention utilizes an inexpensive acid-purging substance (e.g., sodium bicarbonate) to purge acids from the air.

Additionally, the present invention provides for the binding of acid-purging powders to fibers and/or open cell foam which can be industrialized in an inexpensive manner.

And the present invention provides a novel air filter which is particularly advantageous for filtering the air in fumehoods (ductless and/or ducted).

Still other advantages of the aforementioned air filter will be apparent to those skilled in the art in view of the present disclosure.

2. Purging Ammonia and/or Other Target Chemicals from Air

2.1 Difficulties with Purging Ammonia and/or Other Target Chemicals from Air Using Impregnated Activated Carbon Granule Filters Ammonia is one of the most troublesome chemicals present in a laboratory. Among other things, ammonia is highly volatile, has a very low olfactory limit, and is highly detrimental to human health. At the same time, ammonia is also one of the 12 most common chemicals found in a laboratory. For this reason, it is important that there be effective methods and apparatus for protecting laboratory personnel (e.g., chemists, etc.) from the harmful effects of ammonia.

As noted above, because of the harmful properties of ammonia, it is important to protect laboratory personnel from respiratory exposure to ammonia. To this end, filtration fumehoods are commonly used by laboratory personnel to protect themselves from ammonia. In a filtration fumehood (also known as a recirculatory fumehood and/or as a filtering fumehood and/or as a ductless fumehood), impregnated activated carbon granule filters (designed for this specific use) are commonly used to trap ammonia vapors. More particularly, with these activated carbon granule filters, activated carbon granules are impregnated with a chemical specifically chosen for its reaction with ammonia (e.g., sulfuric acid, $ZnCl_2$, etc.). It is necessary to impregnate the activated carbon granules with an ammonia-purging reactant because "classical" (i.e., non-impregnated) activated carbon granules do not efficiently remove ammonia from air. Hence, it is necessary to impregnate the activated carbon granules with an ammonia-purging reactant so as to attract and neutralize the ammonia vapors.

One aspect of this prior art technology of impregnated activated carbon granule filters is that the combined properties of the activated carbon granules, and the ammonia-purging reactant impregnated in the activated carbon granules, allow the neutralization of a small concentration of ammonia per quantity of impregnated activated carbon granules, with a high efficiency (i.e., greater than 99%, if the filter is correctly designed). However, one of the limits of this prior art technology of impregnated activated carbon granule filters is that the chemical (i.e., the ammonia-purging reactant) used for the impregnation loads the porous network of the activated carbon granules, thereby making it impractical to add other neutralizing and/or purging substances to the impregnated activated carbon granule filter. As a result, where the reactant is selected to neutralize ammonia, the impregnated activated carbon granule filter is effectively limited to neutralizing ammonia (and highly related chemicals).

This same problem tends to occur for impregnated activated carbon granule filters which employ other reactants for purging chemicals other than ammonia from the air (e.g., potassium carbonate for purging inorganic acids, etc.).

Thus it will be seen that with impregnated activated carbon granule filters, each filter is effectively limited to handling a short list of chemicals. As a result, the users of filtration fumehoods must select a particular impregnated activated carbon granule filter for their fumehood in accordance with the chemicals that they will be handling in the fumehood, e.g., an activated carbon granule filter impregnated with sulfuric acid for use when handling ammonia, an activated carbon granule filter impregnated with potassium carbonate for use when handling inorganic acids, etc. This can be problematic, since it may require a filter change when different materials are to be handled in the fumehood.

Furthermore, in some cases, there is no appropriate filter for neutralizing the complete array of chemicals that the user will be handling in the fumehood at a particular time. By way of example but not limitation, a chemist who needs to handle an array of acids, bases and solvents cannot currently easily find a single fumehood filter which can simultaneously protect against all of these chemicals.

Thus there is a need for a new and improved filter which can effectively handle a broad range of chemicals which need to be safely handled by laboratory personnel.

2.2 Novel Filter for Purging Ammonia and/or Other Target Chemicals from Air

The present invention also comprises the provision and use of a novel filter for chemical neutralization (and preferably for ammonia vapor neutralization), wherein the novel filter comprises an open cell foam, a reactant (e.g., citric acid for neutralizing ammonia) disposed on the surface of the open cell foam, and glue for holding the reactant (e.g., citric acid) on the surface of the open cell foam.

The open cell foam is preferably formed out of polyurethane (PU), polyethylene (PE), silicone, rubber, polyvinylchloride (PVC) or other material which is resistant to the effects of the target chemical which is to be purged (e.g., ammonia). The open cell foam has a pore size which (a) allows the open cell foam to present a large surface area, and (b) is capable of easily passing air therethrough without imposing a significant pressure drop on the flow of air through the filter, e.g., the open cell foam may have a pore size of 20 pores per inch (PPI).

The reactant is impregnated on the surfaces of the open cell foam so that the reactant is presented to air passing through the open cell foam, whereby to allow the reactant to efficiently react with the target chemical in the air and thereby neutralize the target chemical by virtue of the chemical reaction of the reactant with the target chemical.

In one preferred form of the present invention, the target chemical is ammonia, and the reactant is citric acid.

In one particularly preferred form of the present invention, the citric acid is in granular form, and the citric acid crystals (small grain) are sprinkled directly on the surface of the open cell foam, without requiring that the citric acid be placed in a liquid solution for deployment on the open cell foam (direct sprinkling of citric acid crystals consumes less energy, because it does not require drying, and allows the deposition of a greater quantity of citric acid on the open cell foam). In one preferred form of the present invention, the citric acid crystals have an average grain size majority comprised between 25 ASTM Mesh and 50 ASTM Mesh.

Glue is used to maintain the reactant (e.g., the citric acid crystals) on the surface of the open cell foam. The glue is selected so that the glue does not negatively interact with the open cell foam, and/or with the reactant (e.g., the citric acid), and/or with the target chemical (e.g., ammonia) which is to be filtered from the air. In one preferred form of the present invention, the glue comprises polyvinyl acetate or ethylene vinyl acetate copolymers or acrylic copolymers or other emulsions.

During manufacture, the glue is applied (e.g., by brushing, spraying, etc.) to the open cell foam first, and then the reactant (e.g., citric acid crystals) is applied (e.g., by sprinkling, blowing, etc.) on the surface of the glue-bearing open cell foam.

Figure 6:
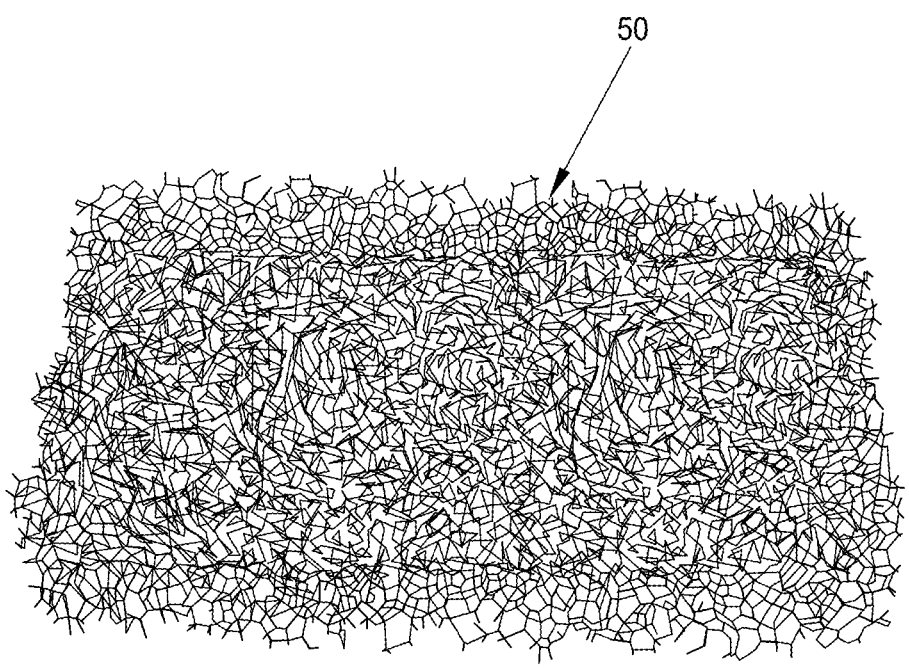
FIG. 6 is a photograph showing a piece of open cell polyurethane (PU) foam before impregnation with granular citric acid crystals.
Figure 7:
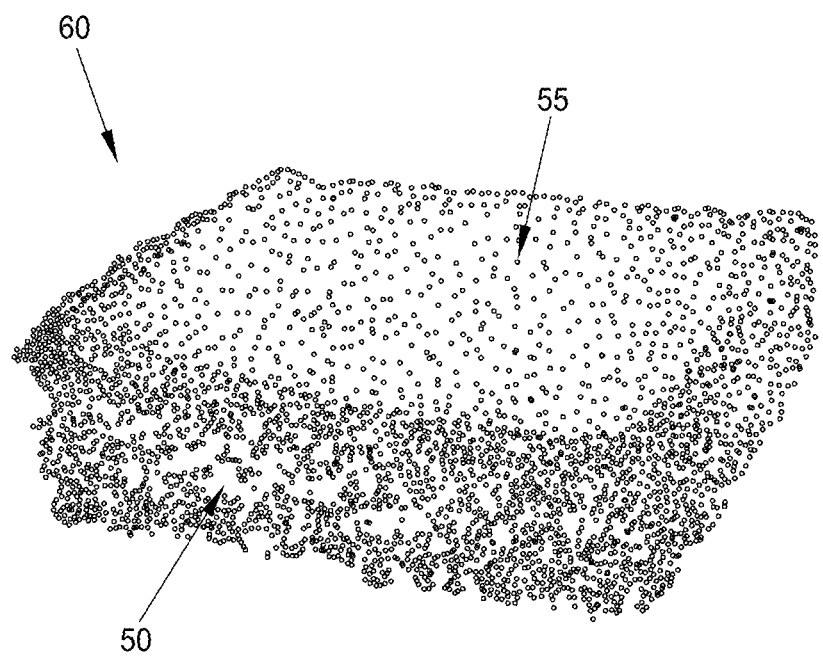
FIG. 7 is a photograph of a piece of open cell polyurethane (PU) foam after the open cell polyurethane (PU) foam has been impregnated with granular citric acid crystals, whereby to form a filter for purging ammonia and/or other target chemicals from air.

See FIG. 6, which is a photograph showing a piece of open cell polyurethane (PU) foam 50 before impregnation with citric acid crystals; and FIG. 7, which is a photograph of a piece of open cell polyurethane (PU) foam 50 after granular citric acid 55 has been deposited on its surfaces, whereby to form a filter 60 for purging ammonia and/or other target chemicals from air.

During use, the target chemical (e.g., ammonia) in the airflow is neutralized on the surface of the open cell foam after a reaction with the reactant (e.g., the citric acid) carried by the open cell foam. In the case of ammonia vapors and citric acid, it is a classical acid-base reaction which leads to the creation of an ammonium citrate salt. This ammonium citrate salt is solid and is retained on the surface of the open cell foam since the citric acid crystals are adhered to the surface of the open cell foam.

It is also possible to form the new filter using a reactant other than citric acid, for purging ammonia vapors and/or other target chemicals from air. By way of example but not limitation, the following alternative acids can be used in place of the aforementioned citric acid: oxalic acid, tartric acid, maleic acid, ascorbic acid, succinic acid, anhydrous phosphoric acid, etc. In this respect it should be appreciated that the reactant (i.e., citric acid or an alternative acid) may be a strong acid or a weak acid. Furthermore, it should also be appreciated that, in addition to its acidic property, the reactant carried by the open cell foam is solid at normal temperature and pressure.

Significantly, and unlike the prior art filters utilizing activated carbon granules, the open cell foam of the present invention can carry multiple reactants for purging multiple target chemicals from the air. Thus, with the present invention, it is not necessary for the filter to be restricted to use for just one target chemical.

2.3 Use of the Novel Filter for Purging Ammonia and/or Other Target Chemicals from Air in Conjunction with Other Filter Stages It should be appreciated that the novel filter for purging ammonia and/or other target chemicals from air can be used alone (e.g., for purging ammonia and/or other target chemicals), or it can be used in combination with other filters (either upstream of, downstream of, or concurrent therewith) to further enlarge the range of target chemicals which can be purged from air.

By way of example but not limitation, the novel filter for purging ammonia and/or other target chemicals of the present invention can be used as one stage of a multi-stage filter, wherein another stage of the multi-stage filter may comprise an activated carbon granule filter (which may or may not be impregnated with a reactant).

By way of further example but not limitation, the novel filter for purging ammonia and/or other target chemicals of the present invention may form one stage of a three-stage filter, i.e., the three-stage filter may comprise an acid-purging stage (e.g., comprising an open cell foam carrying sodium bicarbonate), a solvent-purging stage comprising activated carbon granules, and an ammonia-purging stage comprising an open cell foam carrying citric acid (or an alternative reactant). In this form of the invention, the ammonia-purging stage is preferably placed before the solvent-purging stage, and may be placed before the acid-purging stage if desired.

3. Novel Two-Stage Air Treatment Device Comprising a Non-Thermal Plasma Reactor Stage Followed by a Catalyst Stage 3.1 In General In the foregoing sections, there are disclosed novel filters for use in purging unwanted substances from air. These novel filters may be used individually or in combination with one another (e.g., as individual stages in a multi-stage filter), and may be used to purge acids from air, or to purge solvents from air, or to purge both acids and solvents from air, including to purge ammonia from air. These novel filters are particularly well suited for use in purging unwanted substances from the air of fumehoods before that air is vented, e.g., to the atmosphere (in the case of a ducted fumehood) or to the ambient air of a laboratory containing a fumehood (in the case of a ductless fumehood).

In accordance with the present invention, there is now disclosed another novel device for use in purging unwanted substances from air. This novel device may be used alone, or it may be used in combination with one or more of the filters disclosed hereinabove, or it may be used with one or more other filters or one or more other air treatment devices. Significantly, the novel device hereinafter disclosed is particularly well suited for use in purging unwanted substances from the air of fumehoods before that air is vented, e.g., to the atmosphere (in the case of a ducted fumehood) or to the ambient air of a laboratory containing a fumehood (in the case of a ductless fumehood).

Figure 8:
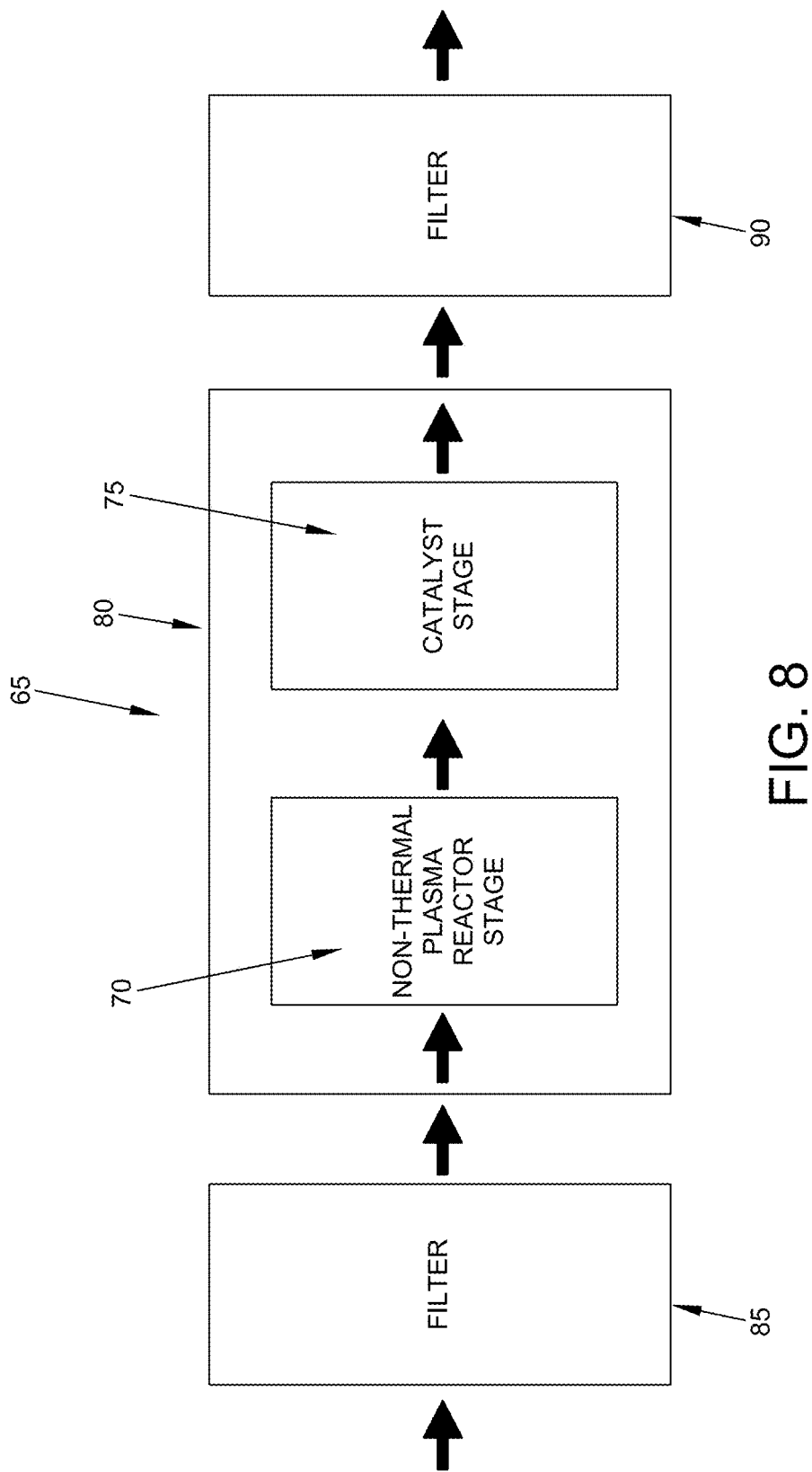
FIG. 8 is a schematic view showing novel apparatus for purging unwanted substances from air, wherein the novel apparatus comprises a novel two-stage air treatment device comprising a non-thermal plasma reactor stage followed by a catalyst stage.
Figure 9:
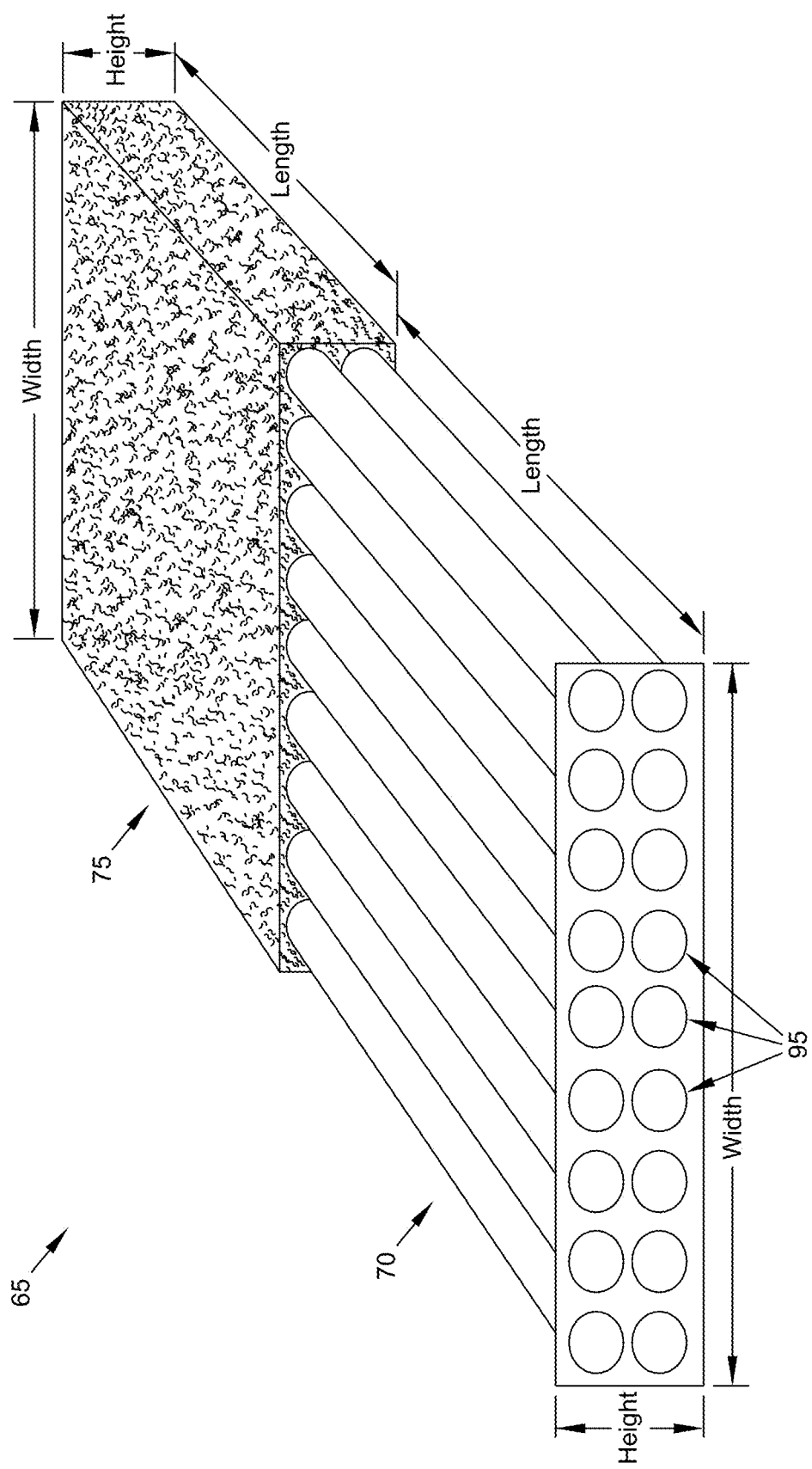
FIGS. 9 and 10 are schematic views of a novel two-stage air treatment device comprising a non-thermal plasma reactor stage followed by a catalyst stage.
Figure 10:
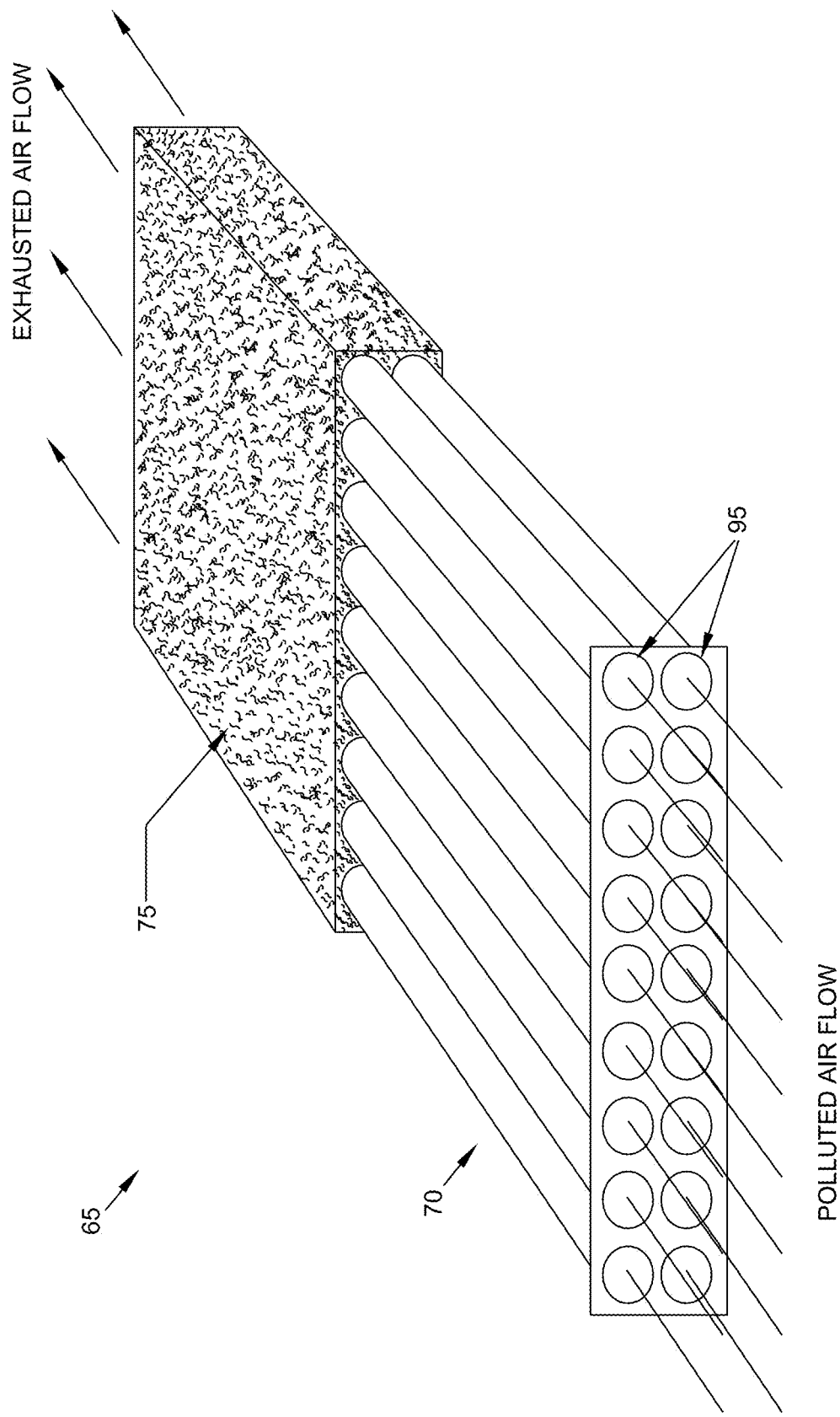

In accordance with the present invention, and looking now at FIGS. 8-10, there is provided a novel two-stage air treatment device 65 which comprises a non-thermal plasma reactor stage 70 followed by a catalyst stage 75. In one form of the invention, non-thermal plasma reactor stage 70 and catalyst stage 75 are contained in a single housing 80 (e.g., a housing sized and configured for appropriate mounting in a fumehood, e.g., a ductless fumehood). Thus, in this form of the invention, two-stage air treatment device 65 comprises an assembly comprising non-thermal plasma reactor stage 70 and catalyst stage 75. If desired, another air treatment device 85 (e.g., a filter) may be disposed upstream of air treatment device 65 in order to treat the air before it enters air treatment device 65, and/or another air treatment device 90 (e.g., a filter) may be disposed downstream of air treatment device 65 in order to treat the air after it leaves air treatment device 65. By way of example but not limitation, air treatment device 85 may comprise one or both stages of the aforementioned air filter 5 (e.g., its acid-purging stage 10 and/or its solvent-purging stage 15) and/or the aforementioned novel filter 60 for purging ammonia and/or other target chemicals from air. By way of further example but not limitation, air treatment device 90 may comprise one or both stages of the aforementioned air filter 5 (e.g., its acid-purging stage 10 and/or its solvent-purging stage 15) and/or the aforementioned novel filter 60 for purging ammonia and/or other target chemicals from air.

The non-thermal plasma reactor stage 70 includes a plurality of non-thermal plasma reactor units 95 (FIGS. 9 and 10) which are designed to oxidize organic molecules exhausted from a filtration fumehood. Note that FIGS. 9 and 10 are intended to be schematic, in the sense that while they show an exemplary configuration of a given Width×Height×Length, other configurations may also be used, depending on the so-called "form factor" of housing 80 (which may itself depend on the form factor of the fumehood with which the novel two-stage air treatment device 65 is used). Each non-thermal plasma reactor unit 95 is preferably optimized to meet the following requirements:

(i) It should be as small as possible in order to be installed in non-thermal plasma reactor stage 70 of two-stage air treatment device 65, which is itself preferably installed on the top of a fumehood enclosure (not shown). In one preferred form of the invention, the maximum dimension of one non-thermal plasma reactor unit 95 should be smaller than 404 mm (Width)×200 mm (Height)×755 mm (Length).

(ii) Each non-thermal plasma reactor unit 95 should preferably be able to treat an airflow of between about 100 m³/h and about 300 m³/h.

(iii) Each non-thermal plasma reactor unit 95 should preferably be able to treat pollutant concentrations of between about 0 ppm and about 200 ppm, with an efficiency higher than 95%. Note: for purposes of the present invention, the efficiency of non-thermal plasma reactor unit 95 is defined as the ratio between (a) the quantity of pollutant totally converted into non-hazardous sub-products, e.g., $CO_2$ and $H_2O$, and (b) the initial quantity of pollutant before introduction into non-thermal plasma reactor unit 95.

(iv) The energy consumption of non-thermal plasma reactor unit 95 should be lower than about 50 J/L of air introduced into non-thermal plasma reactor unit 95.

In order to oxidize the organic pollutants of the air drawn from the fumehood, two-stage air treatment device 65 combines two physical-chemical processes, the first of which is carried out in non-thermal plasma reactor stage 70 and the second of which is carried out in catalyst stage 75:

(i) First, the air from the fumehood passes through a plasma which is created in non-thermal plasma reactor stage 70. More particularly, a plasma is a state of matter similar to gas in which a certain portion of the molecules are ionized. A wide range of different kinds of plasma exist. In the non-thermal plasma reactor units 95 of the present invention, a non-thermal plasma is created, which means that the plasma is created at room temperature. This plasma is created by a discharge generated between two electrodes (see below). When the air from the fumehood passes through the plasma, many by-products are generated, e.g., O•, $O_3$, OH•, etc. These by-products are relatively unstable and reactive, and are used to oxidize the organic pollutants contained in the air drawn from the fumehood, whereby to treat the organic pollutants contained in the air drawn from the fumehood.

(ii) Second, the air from non-thermal plasma reactor stage 70 is passed through a catalyst bed contained in catalyst stage 75 of two-stage air treatment device 65. This latter stage of two-stage air treatment device 65 is used to achieve oxidation of organic pollutants and to destroy residual ozone (created in the preceding non-thermal plasma reactor stage 70) before releasing the treated air from two-stage air treatment device 65 (e.g., for venting to the atmosphere in the case of a ducted fumehood, or for venting to the ambient air of a laboratory in the case of a ductless fumehood), or for passing the treated air to a downstream filter (e.g., filter 90 shown in FIG. 8) for further treatment of the air before venting to the atmosphere or to the ambient air of a laboratory.

3.2 The Non-Thermal Plasma Reactor Stage

Figure 11:
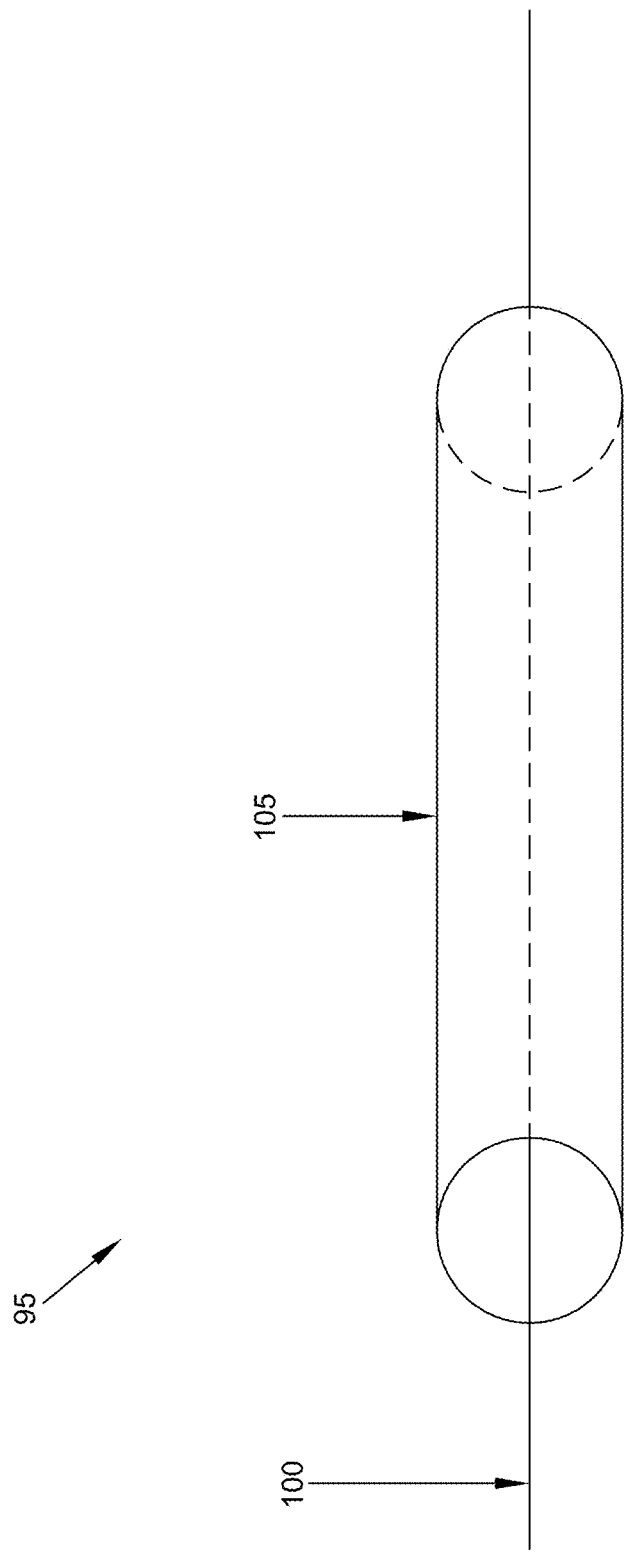
FIGS. 11 and 12 are schematic views showing a non-thermal plasma reactor unit of the sort which may be used in the novel two-stage air treatment device of FIGS. 9 and 10.
Figure 12:
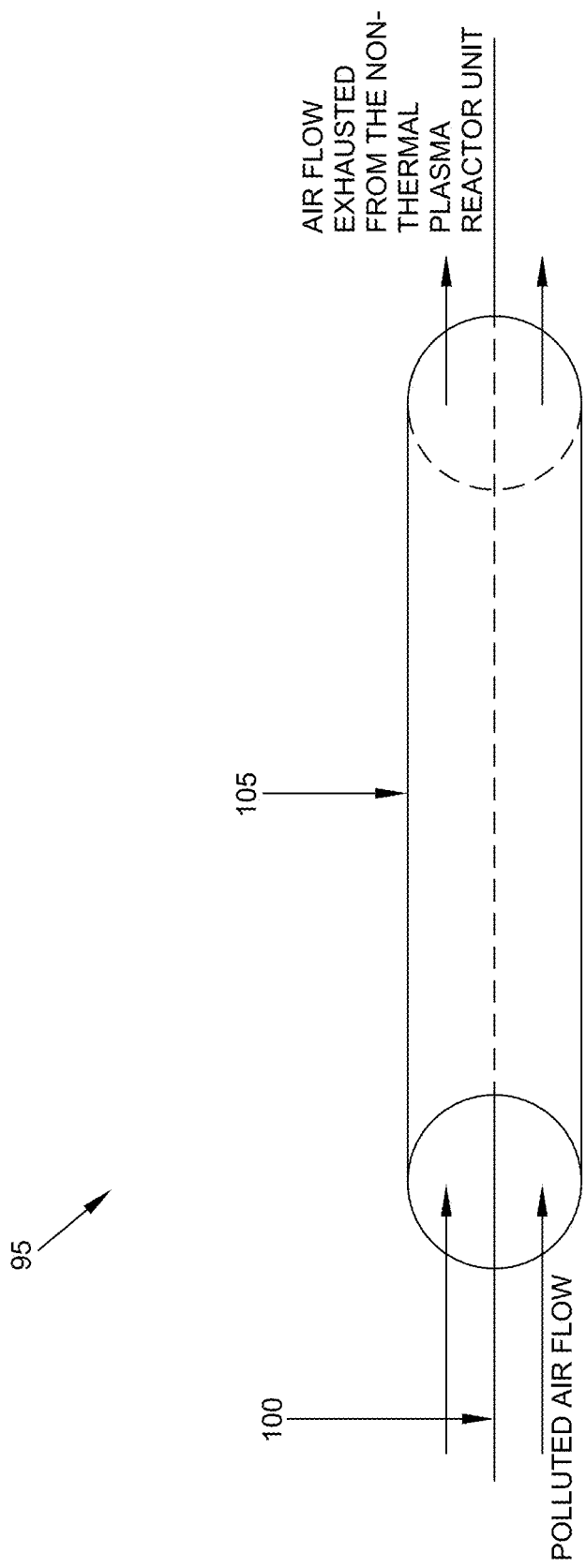

As noted above, non-thermal plasma reactor stage 70 comprises a plurality of non-thermal plasma reactor units 95. In each non-thermal plasma reactor unit 95, a plasma is created between two electrodes. More particularly, and looking now at FIGS. 11 and 12, in one preferred form of the invention, each non-thermal plasma reactor unit 95 of the present invention comprises a so-called "coronal tube" construction, i.e., where non-thermal plasma reactor unit 95 comprises a wire electrode 100 (preferably with a diameter of between about 20 microns and about 60 microns), and a cylinder electrode 105 (preferably with an internal diameter of between about 10 mm and about 30 mm). Various metals may be used to fabricate wire electrode 100 and/or cylinder electrode 105, e.g., copper, iron, stainless steel, tungsten, etc. The length of cylinder electrode 105 is preferably between about 20 cm and about 60 cm. Each non-thermal plasma reactor unit 100 is able to treat an airflow of between 0 and about 100 L/min passing longitudinally through the length of the coronal tube.

In order to treat all of the airflow exhausted from the fumehood, many non-thermal plasma reactor units 95 are assembled together in parallel as shown in FIGS. 9 and 10, whereby to form the complete non-thermal plasma reactor stage 70. This array of parallel coronal tubes preferably has a cross-section (Width×Height) which is equal to the area of the airflow which is to be treated by two-stage air treatment device 65, whereby to ensure maximum treatment of the air.

Figure 14:
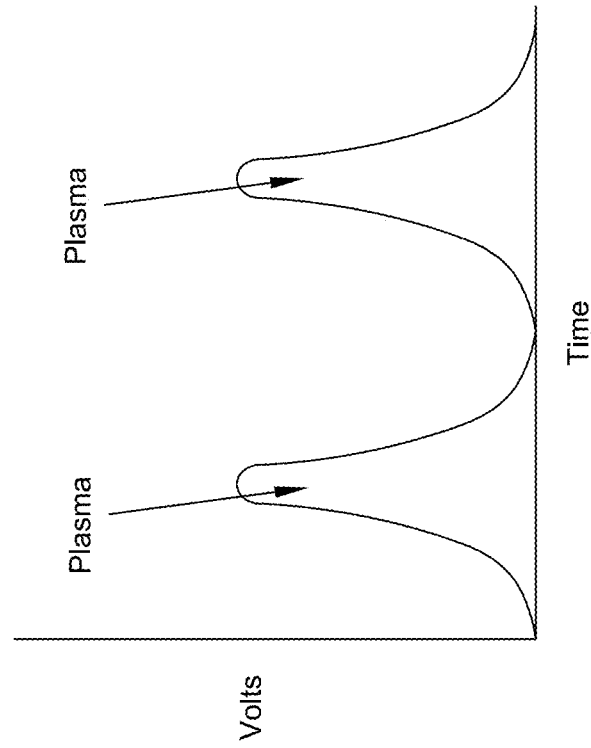
FIGS. 13 and 14 are schematic views showing two different ways of driving the non-thermal plasma reactor unit of FIGS. 11 and 12.
Figure 13:
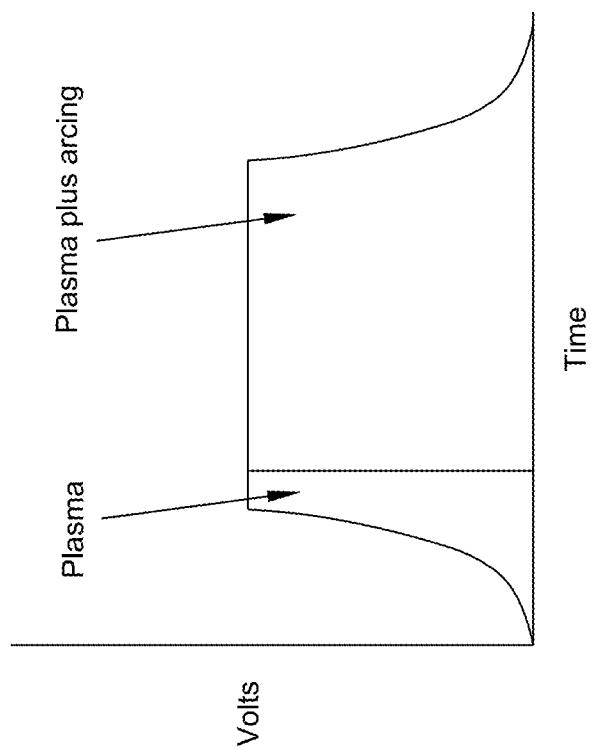

Within the interior of each non-thermal plasma reactor unit 95 (i.e., within the interior of each cylinder electrode 105), a non-thermal plasma is created by applying short electric pulses (preferably approximately 10,000-30,000 V, and preferably approximately 50-2,000 Hz, with the duration of each pulse being about 20 ns at pick middle height). More particularly, when each non-thermal plasma reactor unit 95 comprises a coronal tube construction, it is important to avoid creating an electrical arc within the non-thermal plasma reactor unit 95, since the creation of an electrical arc consumes a large amount of energy and renders the non-thermal plasma reactor stage 70 inefficient. See, for example, FIG. 13, which shows that when the electrical pulses applied to the non-thermal plasma reactor units 95 are not carefully regulated, arcing can occur, with only the leading portion of the electrical pulse being used to create the desired plasma within the non-thermal plasma reactor unit 95 and with the remainder of the electrical pulse creating plasma and arcing. By carefully regulating the electrical pulses applied to non-thermal plasma reactor unit 95, e.g., by keeping the electrical pulses to a short duration such as is shown in FIG. 14, arcing may be effectively eliminated and the non-thermal plasma reactor units 95 driven with significantly higher efficiency.

When the air from the fumehood passes through a non-thermal plasma reactor unit 95, the following reactions (among others) occur:

$$O_2 \rightarrow 2\ O\bullet$$

$$N_2 \rightarrow 2\ N\bullet$$

$$H_2O \rightarrow OH\bullet$$

$$2\ O_2 \rightarrow O_3$$

The by-products that are created in non-thermal plasma reactor unit 95 are relatively unstable, which means that they will react with other molecules present in the air from the fumehood in order to create more stable by-products. Most of the reactions result in an oxidation of the organic pollutants contained in the air from the fumehood, whereby to treat the air from the fumehood.

When air is exhausted from a non-thermal plasma reactor unit 95, it can contain residual $O_3$ (ozone), and by-products of the oxidation of the organic pollutants, and residual concentrations of non-oxidized organic pollutants. This mixture is then treated in the second stage of two-stage air treatment device 65, i.e., catalyst stage 75.

3.3 The Catalyst Stage

Catalyst stage 75 of two-stage air treatment device 65 comprises at least one catalyst and, in a preferred form of the invention, catalyst stage 75 preferably comprises a plurality of different catalysts.

In one preferred form of the invention, catalyst stage 75 comprises $MnO_2$ (manganese dioxide) as a catalyst. The use of $MnO_2$ as a catalyst is highly desirable, since $MnO_2$ promotes the conversion of $O_3$ into $O_2$. This conversion reaction of $O_3$ into $O_2$ will liberate a large amount of O, which is a relatively unstable molecule which will react with other molecules around it, oxidizing them. In other words, the $MnO_2$ catalyst promotes the conversion of $O_3$ so as to liberate a large amount of powerful oxidizers that will react with organic pollutants and organic pollutant by-products in order to convert them into small molecules such as CO, $CO_2$, and $H_2O$. The $MnO_2$ can be supported on various substrates, e.g., ceramic granules, ceramic Raschig rings, open cell foams (e.g., polyurethane, polystyrene, etc.), alumina, activated carbon, charcoal cloths, carbon felt, etc. The $MnO_2$ catalyst can also be nanostructured, i.e., it can be formed as nano-sized clusters on the surface of a substrate (as opposed to being formed as a continuous uninterrupted coating on the surface of a substrate).

In order to limit the exhaust of CO into a closed space (e.g., the ambient air of a laboratory containing a fumehood), it is preferred to use CuO as a second catalyst in catalyst stage 75. Again, the CuO catalyst can be supported on various substrates as discussed above. This CuO catalyst allows the conversion of CO into $CO_2$.

Other catalysts may also be provided in catalyst stage 75, e.g., $CuO_2$, platinum, platinum oxides, gold, etc., and these catalysts may be supported on various substrates as described above.

If desired, the catalysts may be incorporated in a filter element (e.g., activated charcoal granules) so as to simultaneously provide catalyzation and filtration.

Catalyst stage 75 preferably has a "form factor" corresponding to the form factor of non-thermal reactor stage 70 (at least with respect to the cross-section as defined by Width×Height) so as to ensure maximum treatment of the air exiting non-thermal reactor stage 70).

3.4 Alternative Design

Figure 15:
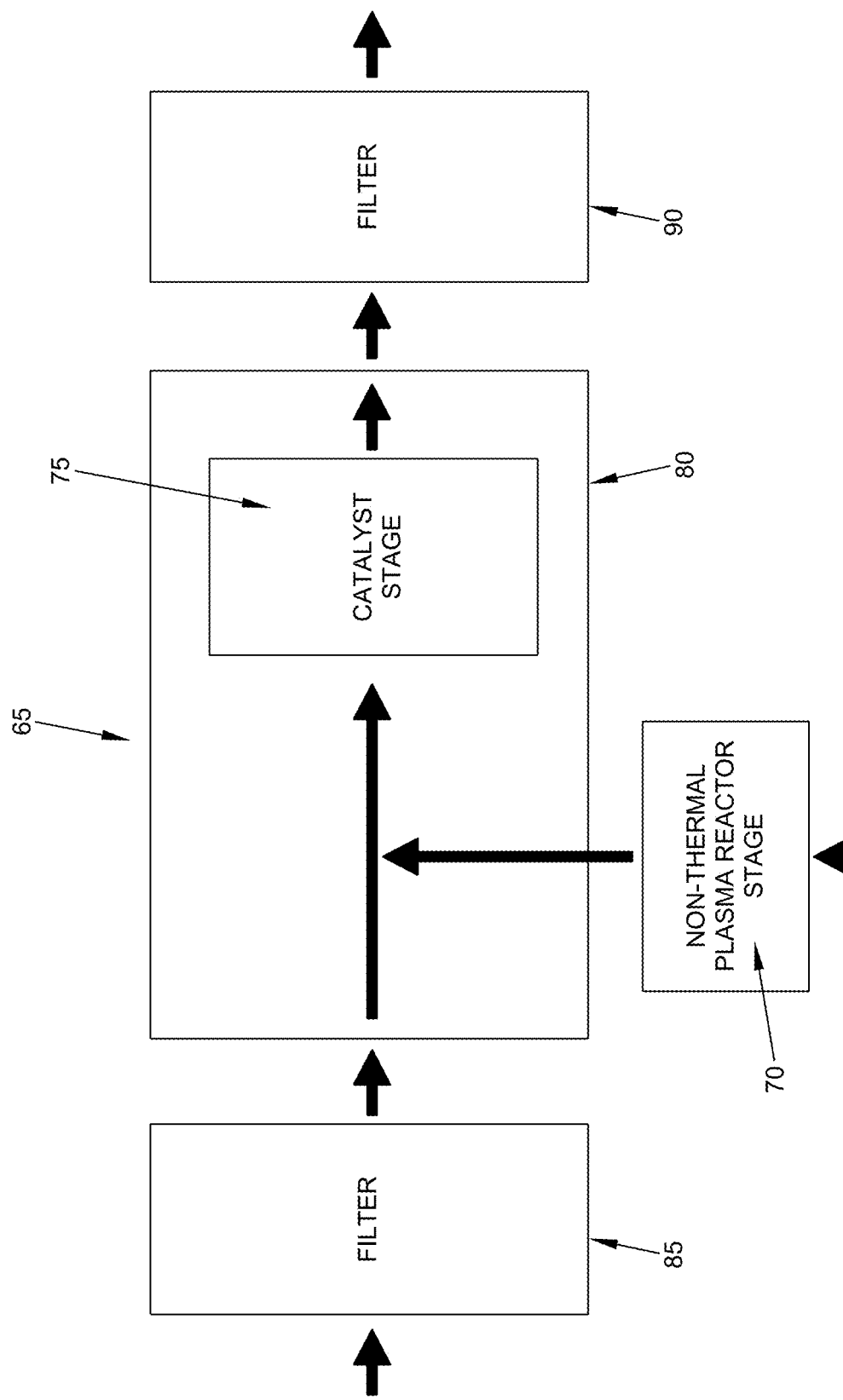
FIG. 15 is a schematic view showing an alternative form of apparatus for purging unwanted substances from air, wherein the novel apparatus comprises a novel two-stage air treatment device comprising a non-thermal plasma reactor stage followed by a catalyst stage.

Looking next at FIG. 15, there is shown an alternative form of the present invention. More particularly, in this form of the invention, non-thermal plasma reactor stage 70 is disposed external to housing 80, with the output of non-thermal plasma reactor stage 70 mixing with the air from the fumehood before entering catalyst stage 75. This design can have certain advantages, e.g., it can be safer since the power source powering non-thermal plasma reactor stage 70 is removed from the airflow from the fumehood (which can contain volatile chemicals), and it can be more efficient since the air entering non-thermal plasma reactor stage 70 can be pre-conditioned to optimize plasma creation (e.g., to remove humidity, which can make it more difficult to create a plasma—in practice, this can be a significant advantage, since the air vented from a fumehood is frequently fairly humid).

It will be appreciated that with the construction shown in FIG. 15, the "form factor" of non-thermal reactor stage 70 (i.e., its Width×Height×Length) may vary from the form factor of housing 80 (i.e., its Width×Height×Length) and/or the form factor of catalyst stage 75 (i.e., its Width×Height×Length).

3.5 Alternative Design for the Non-Thermal Plasma Reactor Stage

In the foregoing discussion, non-thermal plasma reactor stage 70 is described as comprising a plurality of non-thermal plasma reactor units 95, wherein each non-thermal plasma reactor unit 95 comprises a so-called coronal tube construction comprising one wire electrode 100 and one cylinder electrode 105, with the wire electrode being disposed coaxial with, and internal to, cylinder electrode 105. However, as also noted above, when non-thermal plasma reactor units 95 utilize a coronal tube construction, significant care must be taken to tailor the waveform of the electrical pulses driving the non-thermal plasma reactor units 95 in order to avoid the arcing problem discussed above.

Figure 16:
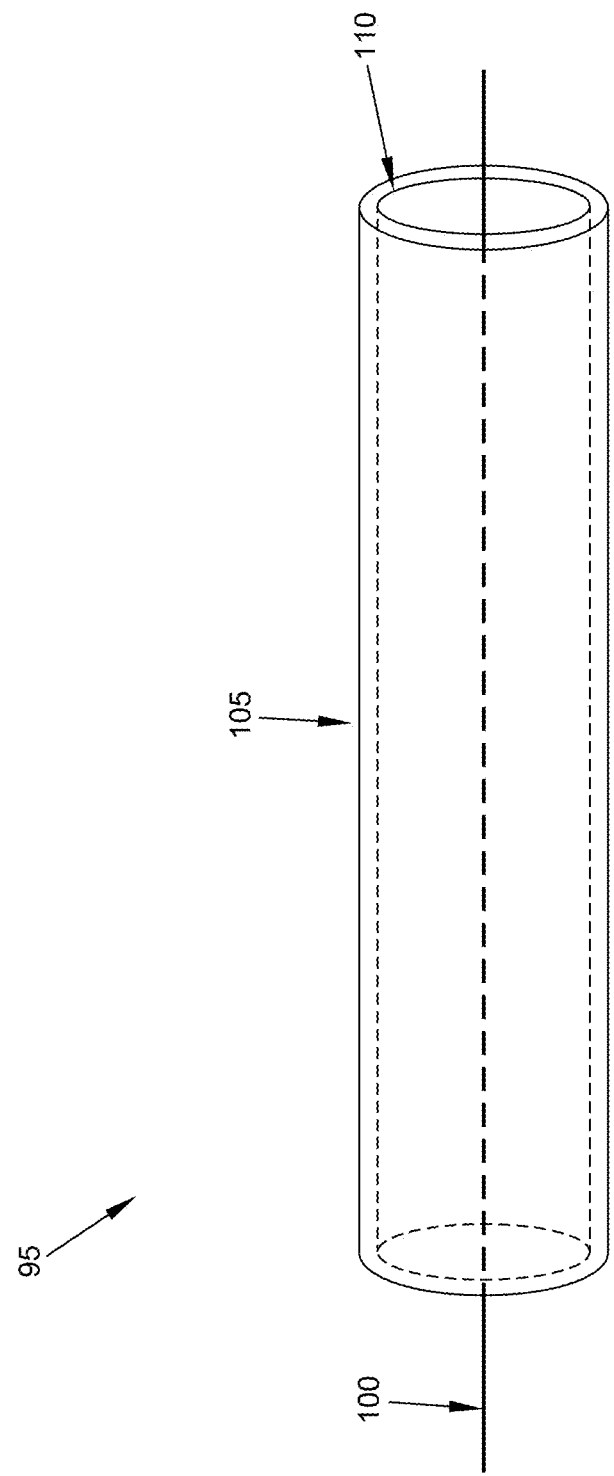

Alternatively, and looking now at FIG. 16, if desired, the non-thermal plasma reactor unit 95 may utilize a so-called dielectric barrier discharge (DBD) construction, where a dielectric tube 110 is disposed coaxial with wire electrode 100 and cylinder electrode 105, with dielectric tube 110 being disposed between wire electrode 100 and cylinder electrode 105. Where the non-thermal plasma reactor unit 95 utilizes a dielectric barrier discharge (DBD) construction, less care must be taken to tailor the waveform of the electrical pulses driving the non-thermal plasma reactor units 95 in order to avoid the arcing problem discussed above.

It is also possible for the non-thermal plasma reactor unit 95 to utilize a dielectric barrier discharge (DBD) construction where one of the electrodes comprises a plate. More particularly, and looking now at FIG. 17, there is shown a non-thermal plasma reactor unit 95 comprising a wire electrode 100 and a plate electrode 115, with wire electrode 100 being separated from plate electrode 115 by a dielectric plate 120.

Figure 17:
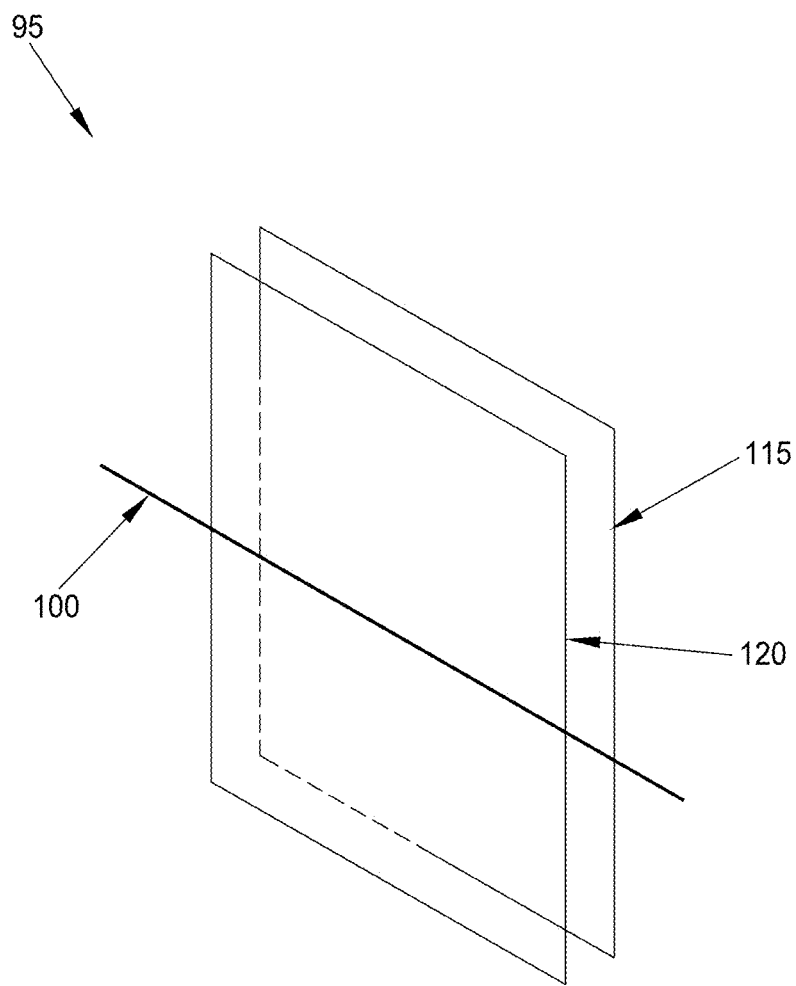

FIG. 17 shows wire electrode 100 being spaced from dielectric plate 120.

Figure 18:
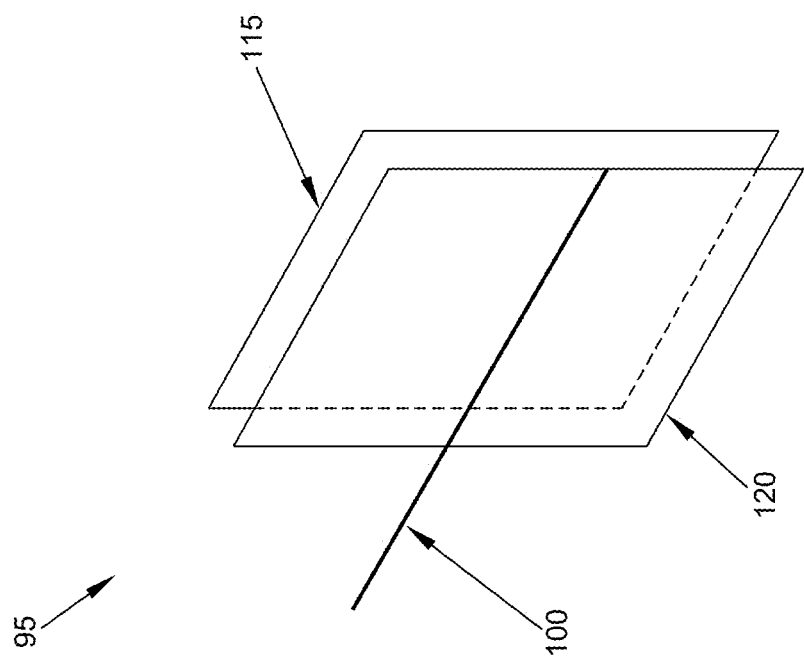

Alternatively, FIG. 18 shows wire electrode 100 being mounted to dielectric plate 120.

Furthermore, it is possible for the non-thermal plasma reactor unit 95 to utilize a dielectric barrier discharge (DBD) construction where both of the electrodes comprises a plate.

More particularly, and looking now at FIG. 19, there is shown a non-thermal plasma reactor unit 95 comprising a first plate electrode 115 and a second plate electrode 125, with first plate electrode 115 being separated from second plate electrode 125 by a dielectric plate 120.

FIG. 20 shows how a plurality of plate-type plasma reactor units 95 may be mounted within a housing 130 so as to constitute a complete non-thermal plasma reactor stage 70. Preferably housing 130 has a cross-section (i.e., Width× Height) corresponding to the area of the airflow which is to be treated by two-stage air treatment device 65, whereby to ensure maximum treatment of the air.

3.6 Substituting Other Ozone Sources for the Non-Thermal Plasma Reactor Stage of the Novel Two-Stage Air Treatment Device In the preceding sections, there is disclosed a novel two-stage air treatment device 65 which comprises a non-thermal plasma reactor stage 70 followed by a catalyst stage 75. In this respect it should be appreciated that a major function of non-thermal plasma reactor stage 70 is to serve as an ozone generator, which then mixes ozone with the air drawn from the fumehood, whereby to treat the organic pollutants contained in the air drawn from the fumehood, before the molecules are passed through catalyst stage 75. With this in mind, it should be appreciated that it is also possible to substitute other ozone sources for non-thermal plasma reactor stage 70 of novel two-stage air treatment device 65.

Thus, in another form of the present invention, the novel two-stage air treatment device may comprise an ozone source stage followed by a catalyst stage, where the ozone source comprises an ozone generator other than the non-thermal plasma reactor stage 70 described above.

3.7 Using the Two-Stage Air Treatment Device in Conjunction with Filters and/or Other Devices The two-stage air treatment device 65 of the present invention may be used alone to treat the air of a fumehood, or it may be used in conjunction with filters and/or other devices. Thus, for example, in one preferred form of the invention, and looking now at FIGS. 8 and 15, the air from the fumehood may be passed through another air treatment device 85 (e.g., a filter) before it is introduced into two-stage air treatment device 65, and/or the air exiting two-stage air treatment device 65 may be passed through another air treatment device 90 (e.g., a filter) before being vented to the atmosphere (in the case of a ducted fumehood) or to the ambient air of a laboratory (in the case of a ductless fumehood).

In one preferred form of the present invention, air is passed through a filter 85 before it is introduced into air treatment device 65, so as to remove selected substances from the air using filter technology, and then it is passed through air treatment device 65, thereby improving the efficiency of air treatment device 65. By way of example but not limitation, filter 85 may comprise an activated carbon granule filter for removing various substances (e.g., benzene, isopropyl alcohol, etc.) from the air before the air is introduced into air treatment device 65. This improves the efficiency of air treatment device 65, because then air treatment device 65 only needs to deal with a smaller number of pollutants. And in one preferred form of the invention, the air exiting air treatment device 65 is passed through another filter 90 before being vented to the atmosphere (in the case of a ducted fumehood) or to the ambient air of a laboratory (in the case of a ductless fumehood).

MODIFICATIONS OF THE INVENTION

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An air treatment device for purging unwanted substances from air, the air treatment device comprising:
a treatment passageway having an upstream end for admitting the air which is to be treated and a downstream end for discharging the air which has been treated;
a side passageway communicating with the treatment passageway intermediate the upstream end of the treatment passageway and the downstream end of the treatment passageway;
a non-thermal plasma reactor stage disposed in the side passageway, wherein the non-thermal plasma reactor stage comprises a plurality of non-thermal plasma reactor units, wherein each of the plurality of non-thermal plasma reactor units comprises a dielectric barrier discharge (DBD) construction comprising a first electrode and a second electrode, wherein each of the plurality of non-thermal plasma reactor units is configured to generate a plasma between the first electrode and the second electrode, whereby when the air which is to be treated passes through the plasma, air byproducts comprising $O_3$ and CO are generated; and
a catalyst stage disposed within the treatment passageway downstream of the non-thermal plasma reactor stage, wherein the catalyst stage comprises (i) $MnO_2$ for converting the $O_3$ generated by the plasma into $O_2$ and (ii) CuO for converting the CO generated by the plasma into $CO_2$.

2. An air treatment device according to claim 1 wherein the first electrode of the dielectric barrier discharge (DBD) construction comprises a first plate electrode and the second electrode of the DBD construction comprises a second plate electrode, and further wherein a plate dielectric is disposed between the first plate electrode and the second plate electrode.

3. The air treatment device according to claim 1 wherein the plurality of non-thermal plasma reactor units are assembled together in parallel.

4. The air treatment device according to claim 1 wherein a dielectric plate is disposed between the first electrode and the second electrode.

5. The air treatment device according to claim 4 wherein at least one of the first and second electrodes is mounted to the dielectric plate.

6. An air treatment device according to claim 1, wherein the non-thermal plasma reactor unit comprises a wire electrode, a cylinder electrode disposed around the wire electrode, and a cylinder dielectric disposed between the wire electrode and the cylinder electrode.

7. An air treatment device according to claim 6 wherein the wire electrode, the cylinder electrode and the cylinder dielectric are disposed coaxially.

8. An air treatment device according to claim 1, wherein the non-thermal plasma reactor unit comprises a wire electrode, a plate electrode, and a plate dielectric disposed between the wire electrode and the plate electrode.

9. The air treatment device according to claim 2 wherein a potential difference applied across the first plate electrode and the second plate electrode comprises electric pulses at a frequency of 50 Hz to 2000 Hz.

10. An air treatment device according to claim 1 further comprising a filter located upstream of the non-thermal plasma reactor stage.

11. An air treatment device according to claim 1, further comprising a filter located downstream of the catalyst stage.

* * * * *